United States Patent [19]
Herekar et al.

[11] Patent Number: 6,149,643
[45] Date of Patent: Nov. 21, 2000

[54] METHOD AND APPARATUS FOR EXPOSING A HUMAN EYE TO A CONTROLLED PATTERN OF RADIATION

[75] Inventors: Satish V. Herekar, Palo Alto; Benjamin W. Woodward, Santa Clara, both of Calif.

[73] Assignee: Sunrise Technologies International, Inc., Fremont, Calif.

[21] Appl. No.: 09/146,999

[22] Filed: Sep. 4, 1998

[51] Int. Cl.⁷ .................................................. A61B 18/18
[52] U.S. Cl. ................................... 606/5; 606/4; 606/17; 606/10
[58] Field of Search ................................ 606/5–6, 4, 107, 606/166, 10, 13, 17, 18; 128/898; 351/245

[56] References Cited

U.S. PATENT DOCUMENTS

| | | |
|---|---|---|
| 4,538,608 | 9/1985 | L'Esperance . |
| 4,884,884 | 12/1989 | Werner . |

(List continued on next page.)

FOREIGN PATENT DOCUMENTS

| | | |
|---|---|---|
| 0467775 | 1/1992 | European Pat. Off. . |
| 0503802A1 | 9/1992 | European Pat. Off. . |
| 4308447 | 9/1994 | Germany . |
| 4338240 | 5/1995 | Germany . |
| WO8707829 | 12/1987 | WIPO . |
| WO8907920 | 9/1989 | WIPO . |
| WO9011054 | 10/1990 | WIPO . |
| WO9316631 | 9/1993 | WIPO . |
| WO9403134 | 2/1994 | WIPO . |
| WO9425836 | 11/1994 | WIPO . |
| WO9527534 | 10/1995 | WIPO . |
| WO9818522 | 5/1998 | WIPO . |
| WO9819741 | 5/1998 | WIPO . |
| WO9822055 | 5/1998 | WIPO . |

OTHER PUBLICATIONS

Rovetta, A., et al., "Telerobotics Surgery in a Transatlantic Experiment: Application in Laparoscopy," *SPIE*, vol. 2057, pp. 337–344, (Apr., 1993).

International Search Report for PCT/US 99/19961 dated Apr. 28, 2000.

International Search Report for PCT/US/99/19961 dated Jan. 12, 2000.

Neumann et al. "Effect of Thermokeratoplasty on Corneal Curvature" Journal of Cataract Refractive Surgery, vol. 16, pp. 727–731, Nov. 1990.

(List continued on next page.)

*Primary Examiner*—Linda C. M. Dvorak
*Assistant Examiner*—A. Farah
*Attorney, Agent, or Firm*—Majestic, Parsons, Siebert & Hsue PC

[57] ABSTRACT

An instrument primarily adapted for use in photothermal keratoplasty procedures to shrink collagen tissue within a cornea of an eye being treated by controlled heating of the tissue with infra-red radiation. In a specific implementation example, a moveable multi-faceted prism is a primary optical element that forms a desired treatment infra-red radiation pattern from a single beam source. Multiple exposures to variations of the radiation pattern are provided. Parameters of two or more exposures to spot radiation patterns are stored in a memory of the instrument, and automatically configure the instrument to deliver the two or more exposures in sequence. Automatic calibration of the radiation intensity is also provided. A guide positions the head of the patient with respect to the instrument, and sensors monitoring movement of both the head and eye provide signals used to by the instrument to control radiation delivery. Connection of a number of instruments over the Internet to a central computer system allows maintaining a central patient treatment database, storing data of any instrument failures or faults useful for instrument maintenance and charging the instrument users for the individual procedures performed. A smart card is also useable as a prepayment device to authorize treatments to be performed by the instrument, and data from the treatment may also be recorded on the smart card.

13 Claims, 16 Drawing Sheets

U.S. PATENT DOCUMENTS

| | | |
|---|---|---|
| 4,887,019 | 12/1989 | Reis et al. . |
| 4,887,592 | 12/1989 | Loertscher . |
| 4,976,709 | 12/1990 | Sand .............. 606/5 |
| 5,000,563 | 3/1991 | Gisel et al. .............. 351/245 |
| 5,002,386 | 3/1991 | Reis et al. . |
| 5,051,564 | 9/1991 | Schmidt . |
| 5,098,426 | 3/1992 | Sklar et al. .............. 606/5 |
| 5,137,530 | 8/1992 | Sand . |
| 5,146,067 | 9/1992 | Sloan et al. . |
| 5,152,759 | 10/1992 | Parel et al. . |
| 5,163,934 | 11/1992 | Munnerlyn .............. 606/5 |
| 5,258,906 | 11/1993 | Kroll et al. . |
| 5,263,951 | 11/1993 | Spears et al. . |
| 5,281,211 | 1/1994 | Parel et al. . |
| 5,304,169 | 4/1994 | Sand .............. 606/5 |
| 5,318,047 | 6/1994 | Davenport et al. .............. 128/898 |
| 5,334,190 | 8/1994 | Seiler .............. 606/5 |
| 5,348,551 | 9/1994 | Spears et al. . |
| 5,367,464 | 11/1994 | Abumehdi et al. . |
| 5,376,086 | 12/1994 | Khoobehi et al. .............. 606/4 |
| 5,395,356 | 3/1995 | King et al. .............. 606/4 |
| 5,437,658 | 8/1995 | Muller et al. .............. 606/5 |
| 5,439,462 | 8/1995 | Bille et al. .............. 606/6 |
| 5,520,679 | 5/1996 | Lin . |
| 5,556,395 | 9/1996 | Shimmick et al. .............. 606/4 |
| 5,569,238 | 10/1996 | Shei et al. .............. 606/4 |
| 5,618,248 | 4/1997 | Sand .............. 606/5 |
| 5,779,696 | 7/1998 | Berry et al. . |

OTHER PUBLICATIONS

Cartlidge et al., "A laser surgical unit for Photoablative and Photothermal Keratoplasty", SPIE, vol. 1423, pp. 167–175, Jan. 21, 1991.

Thompson et al., "Therapeutic and Diagnostic Application of Lasers in Ophthalmology", Proceedings of the IEEE, vol. 80, No. 6, pp. 838–860, Jun. 1992.

Durrie et al., "Application of the holmium: YAG laser for refractive surgery", Reprint of paper to be published in SPIE Proceedings, 644, Nov. 1992.

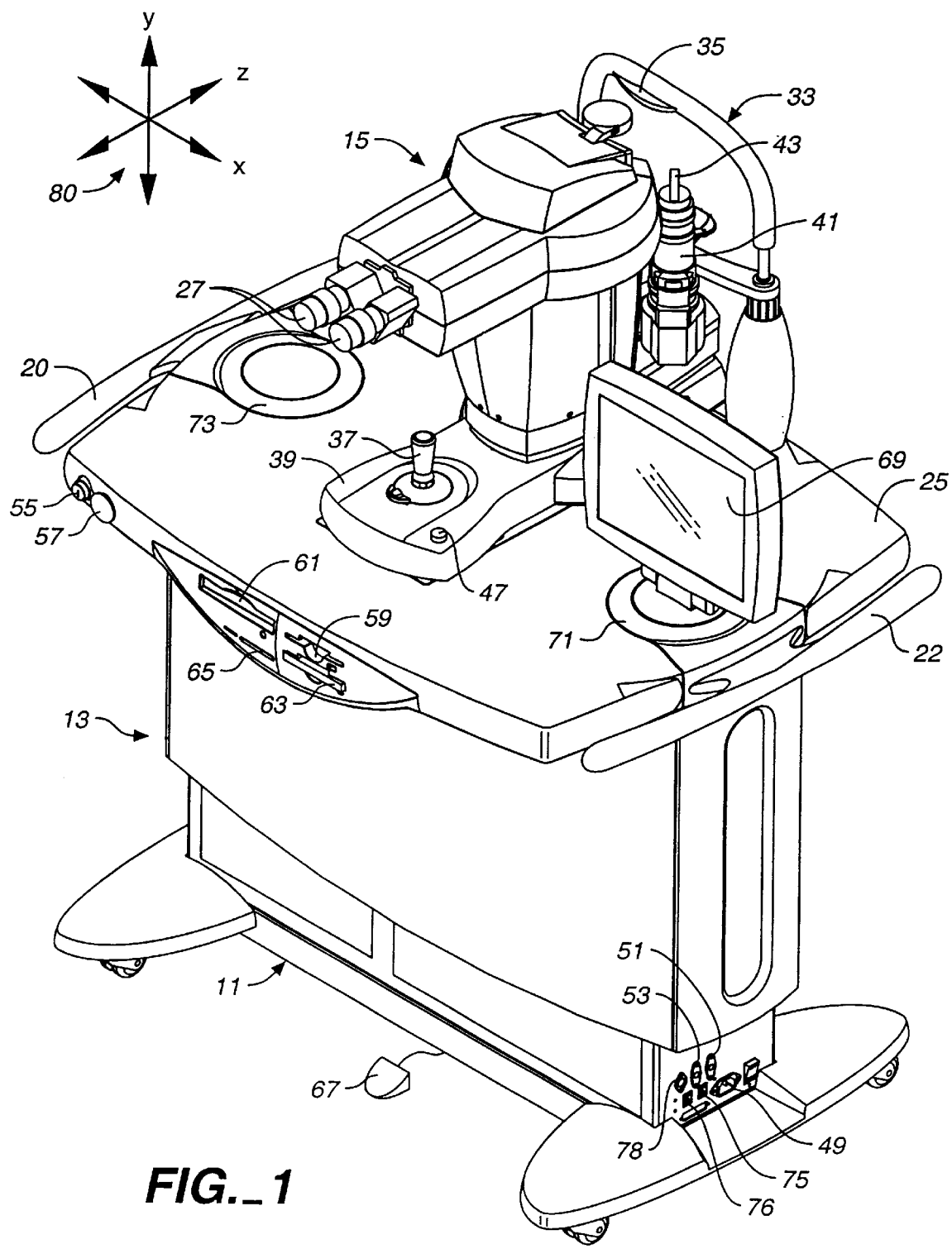
FIG._1

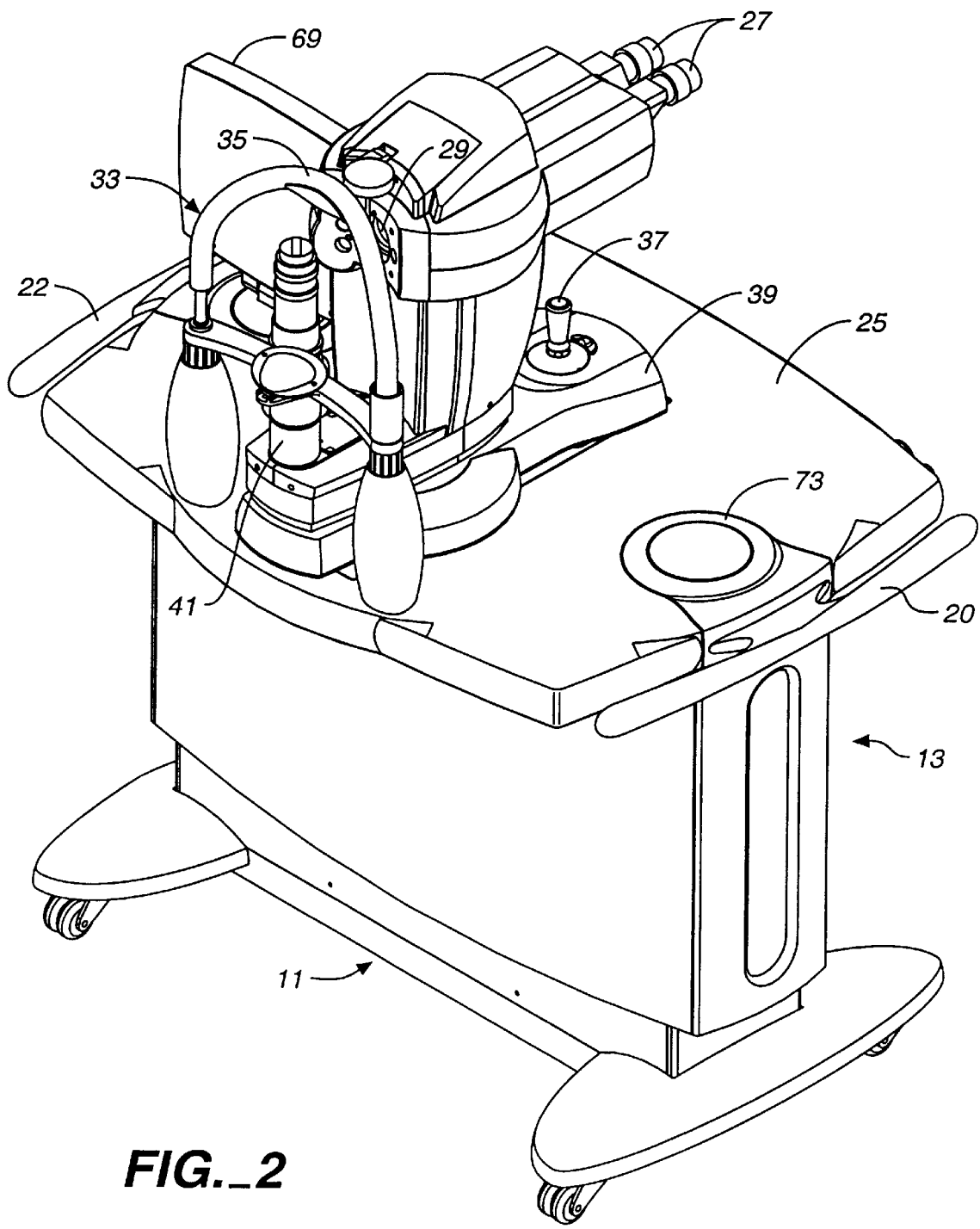
FIG._2

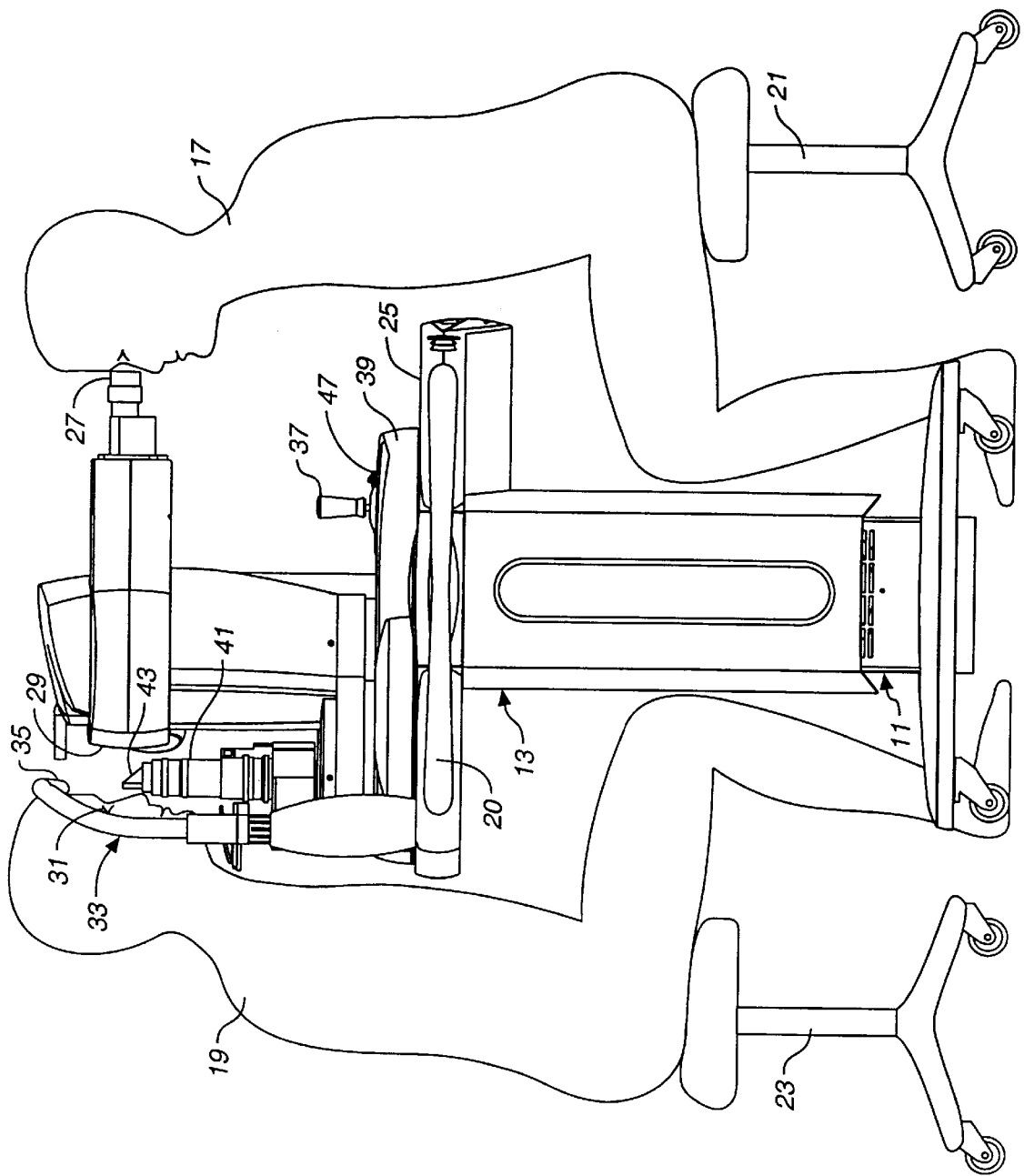
FIG._3

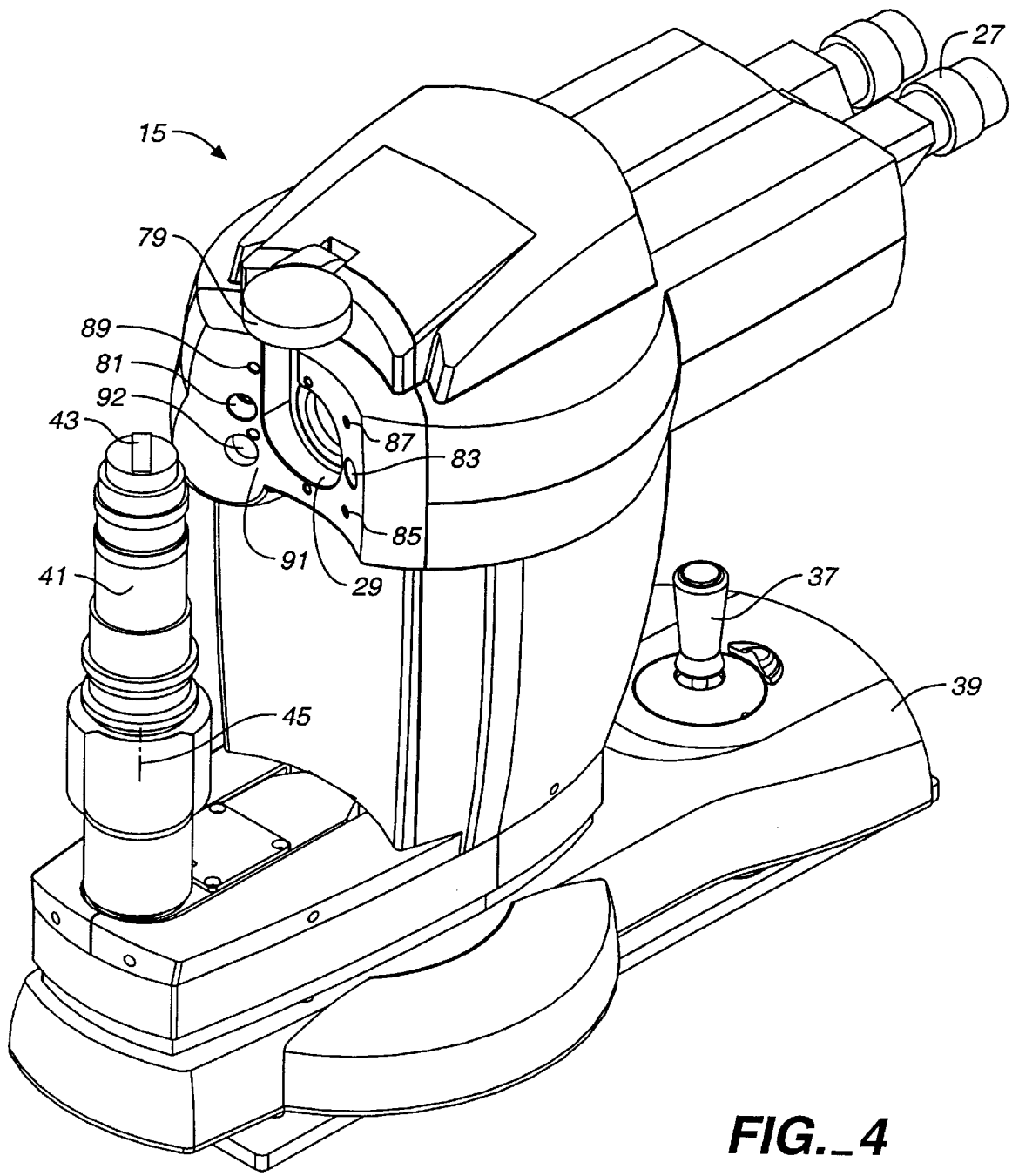
FIG._4

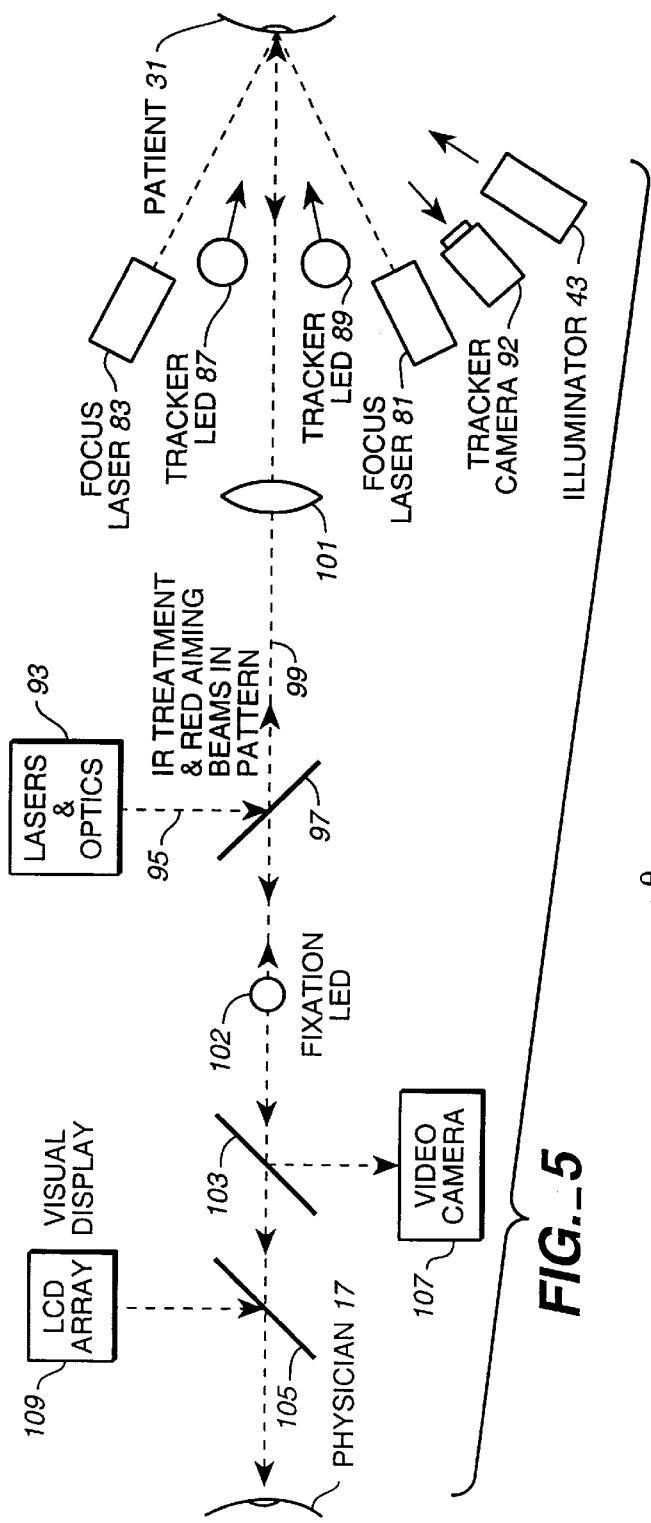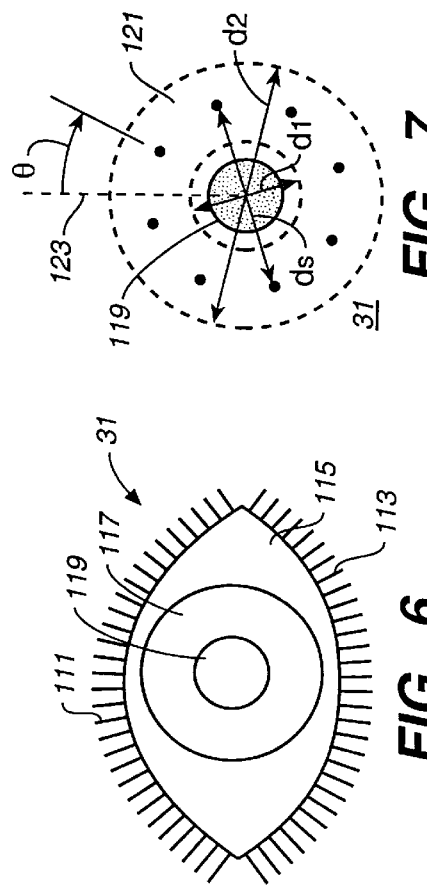

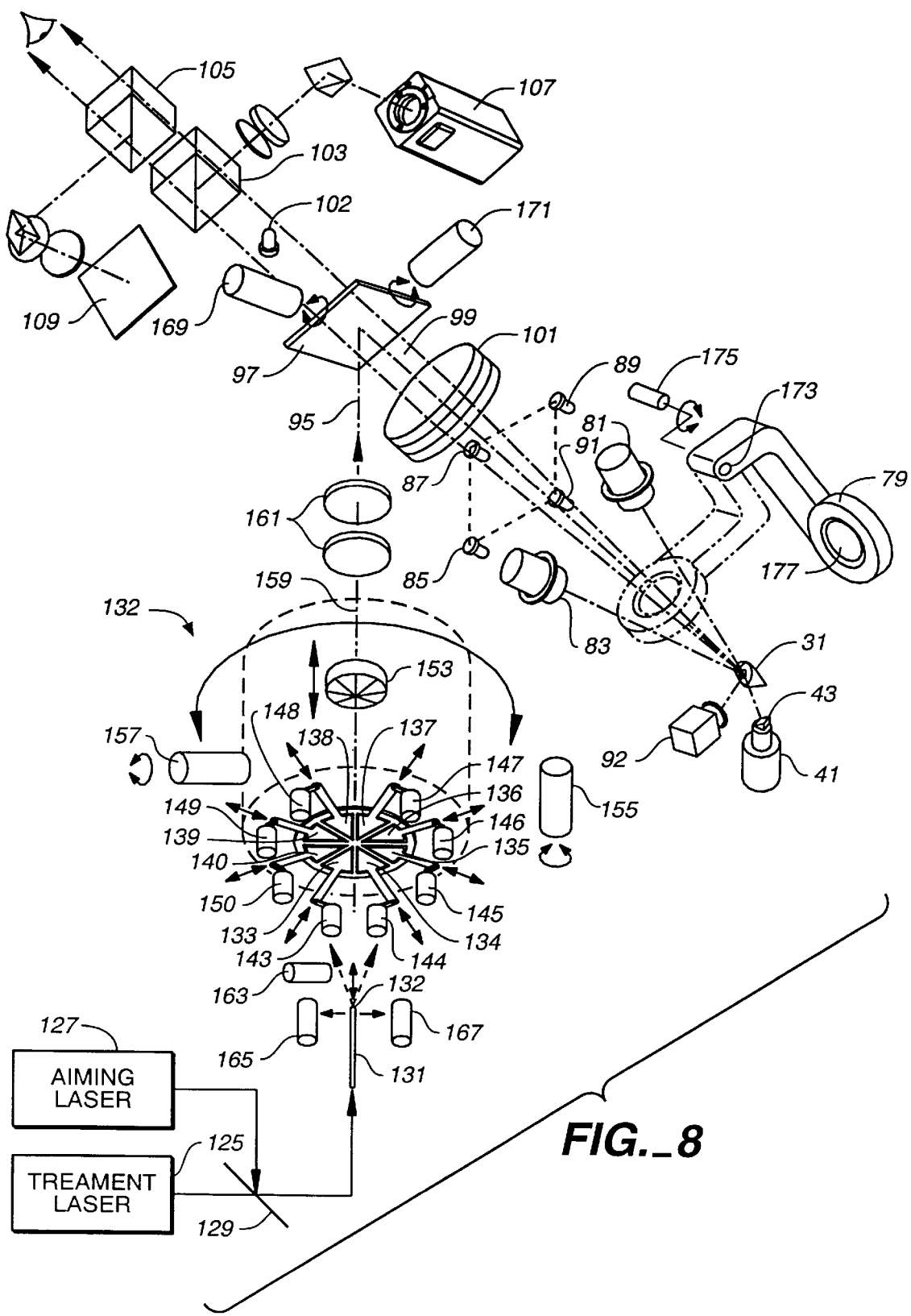
FIG._8

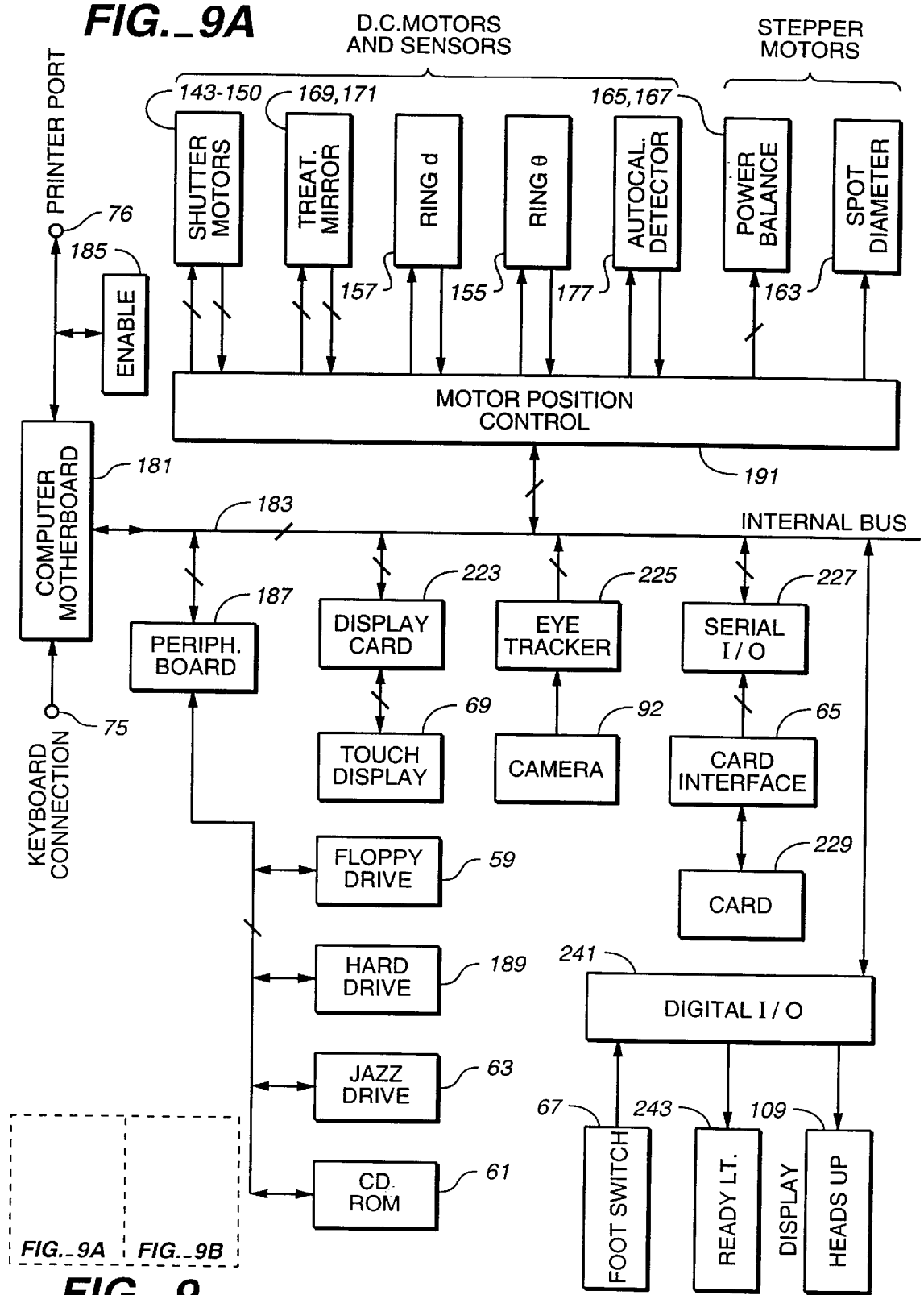

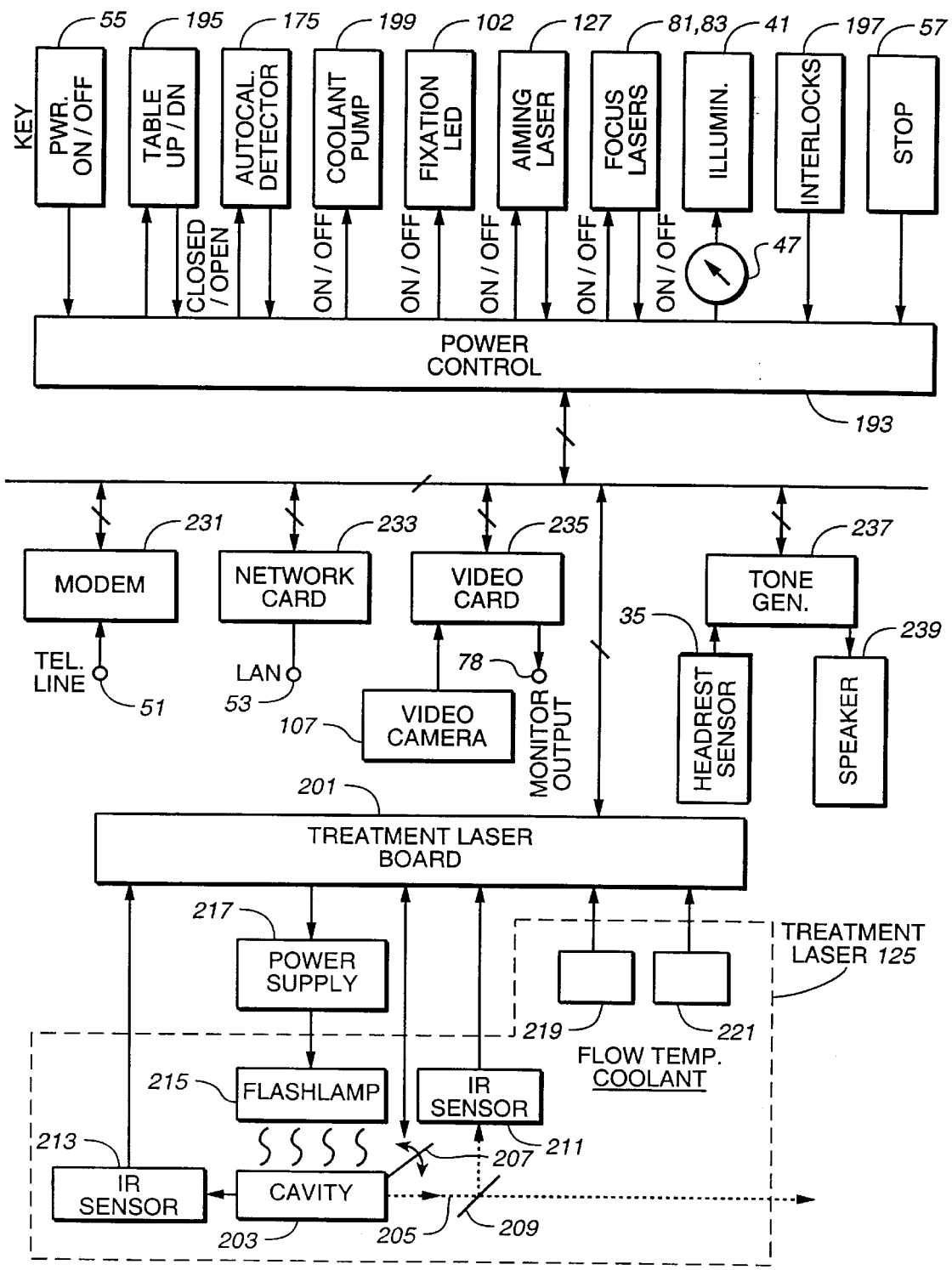
FIG._9B

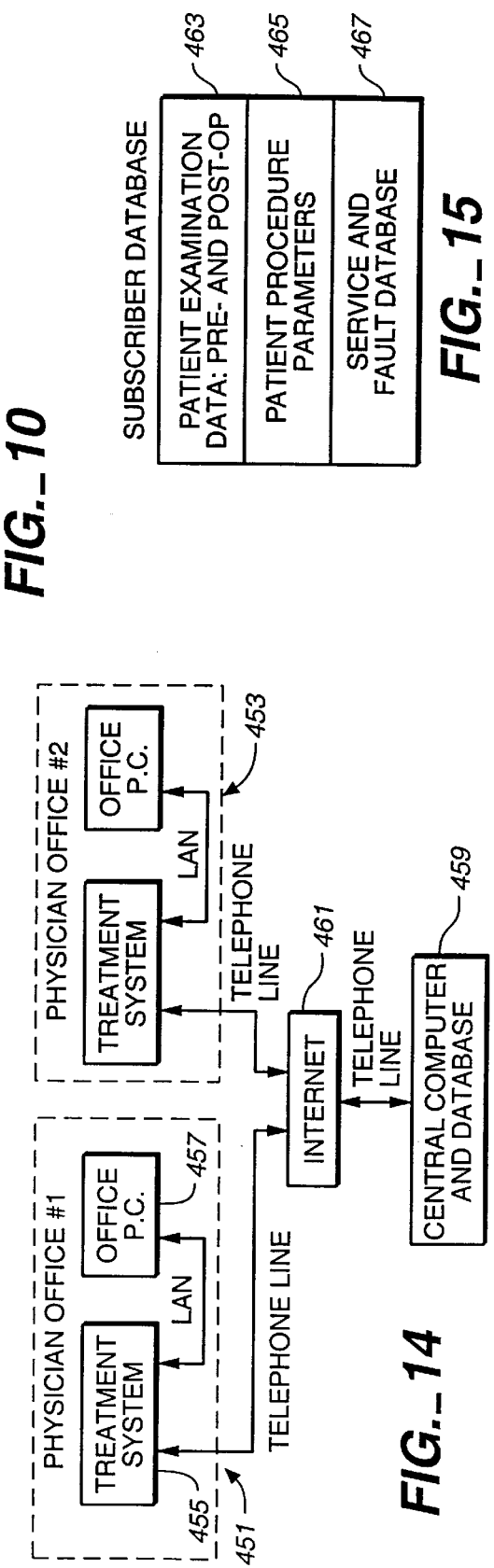
FIG._10
FIG._15
FIG._14

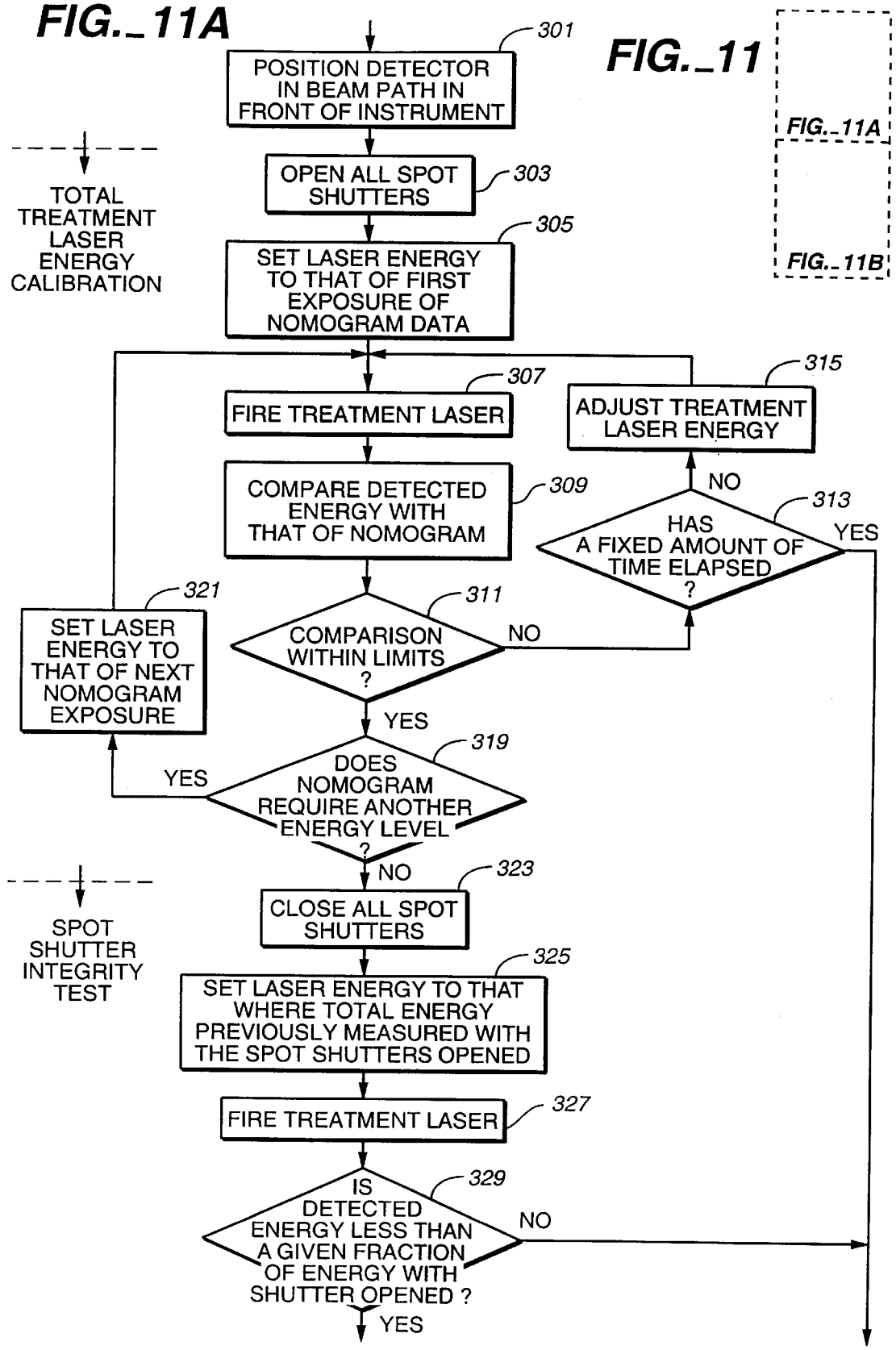

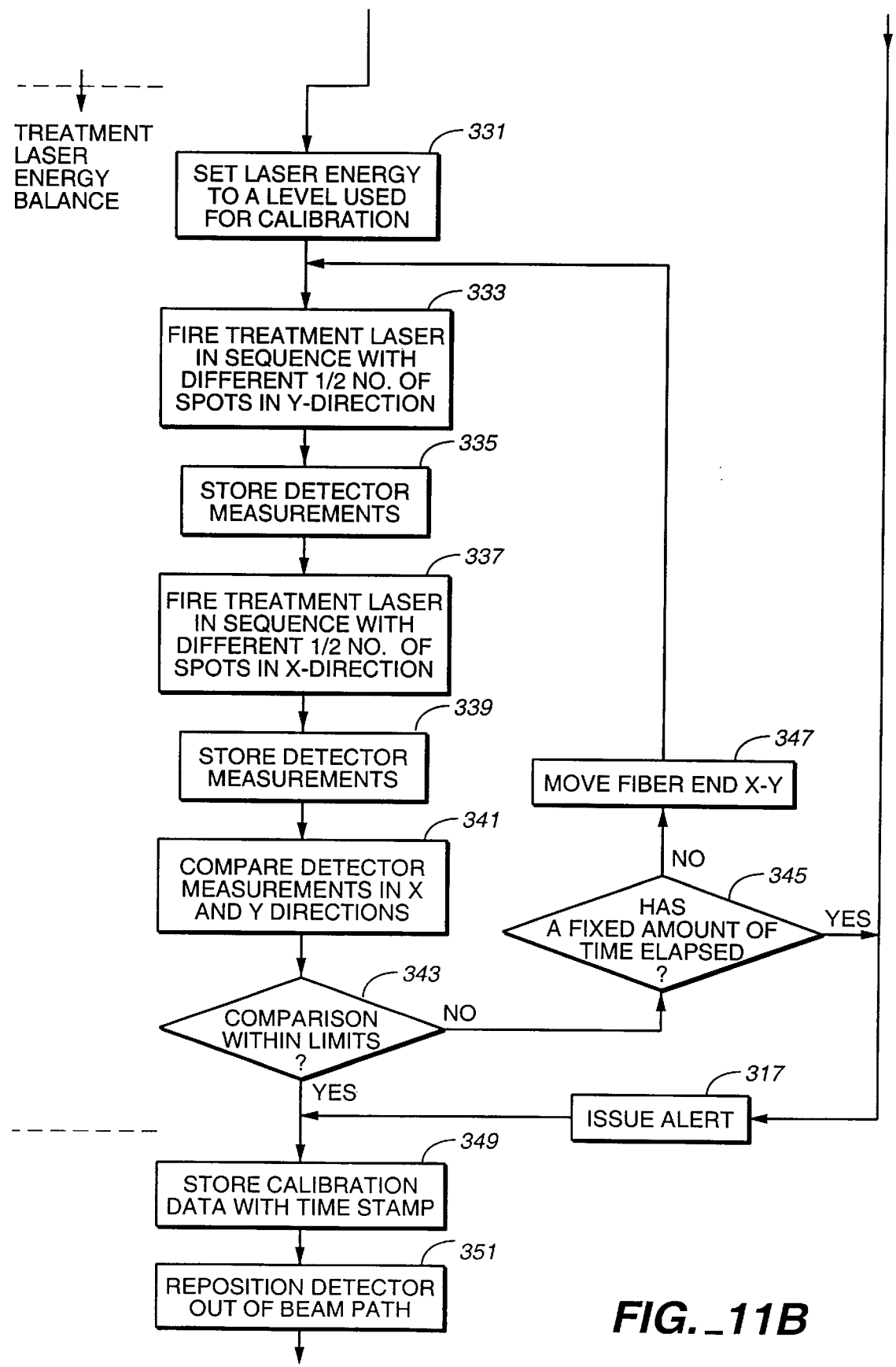
FIG._11B

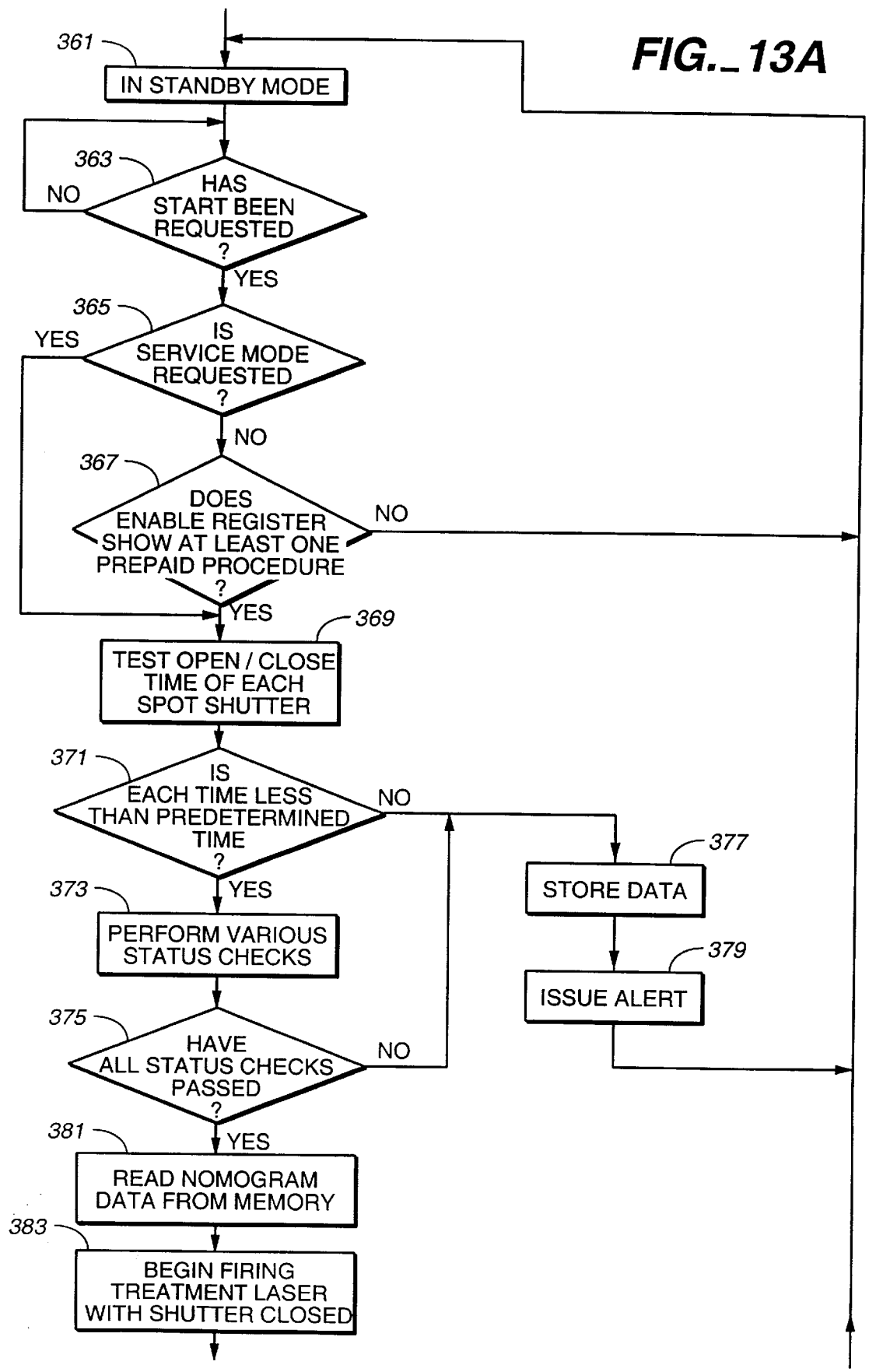
FIG._13A

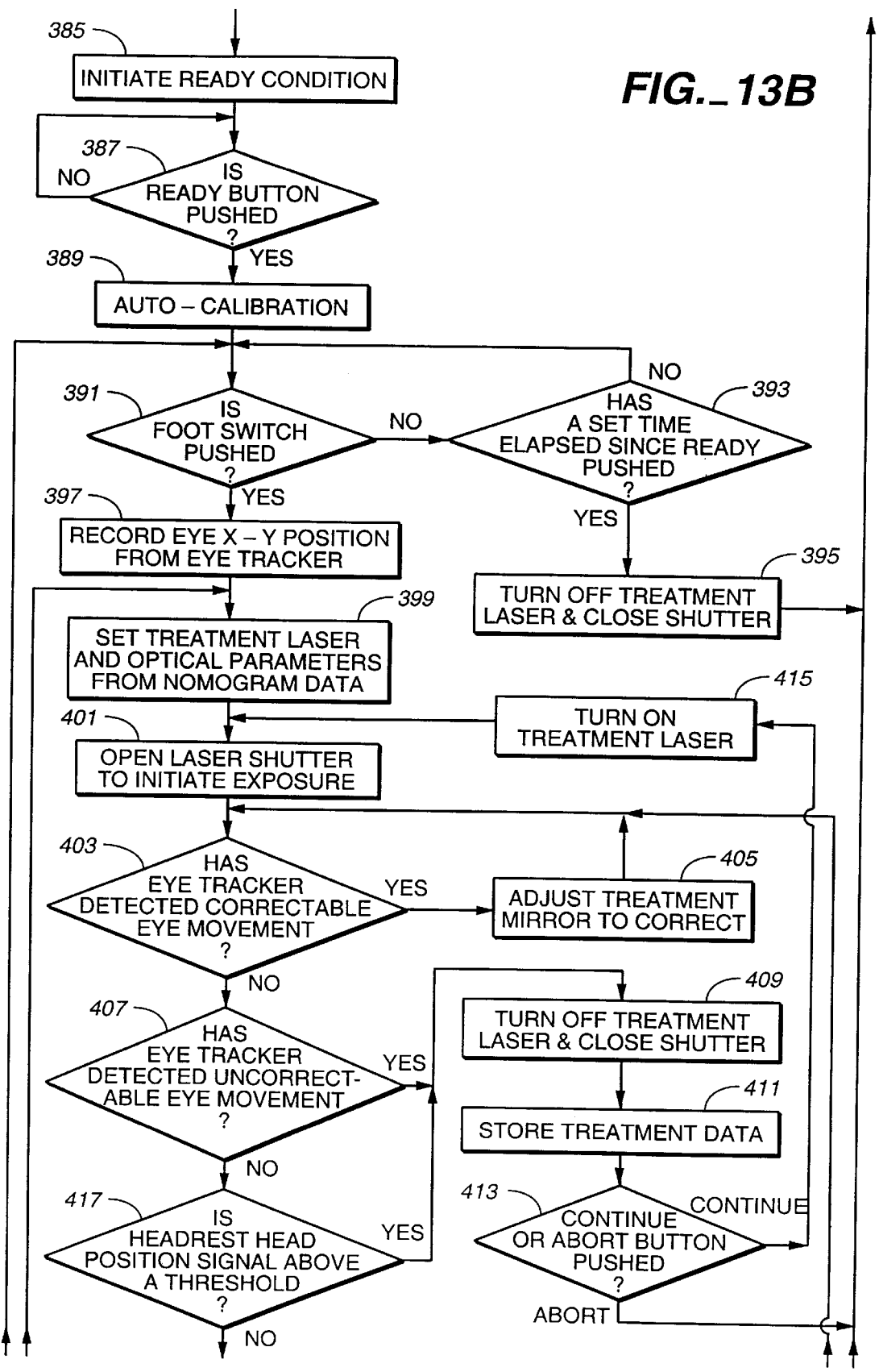
FIG._13B

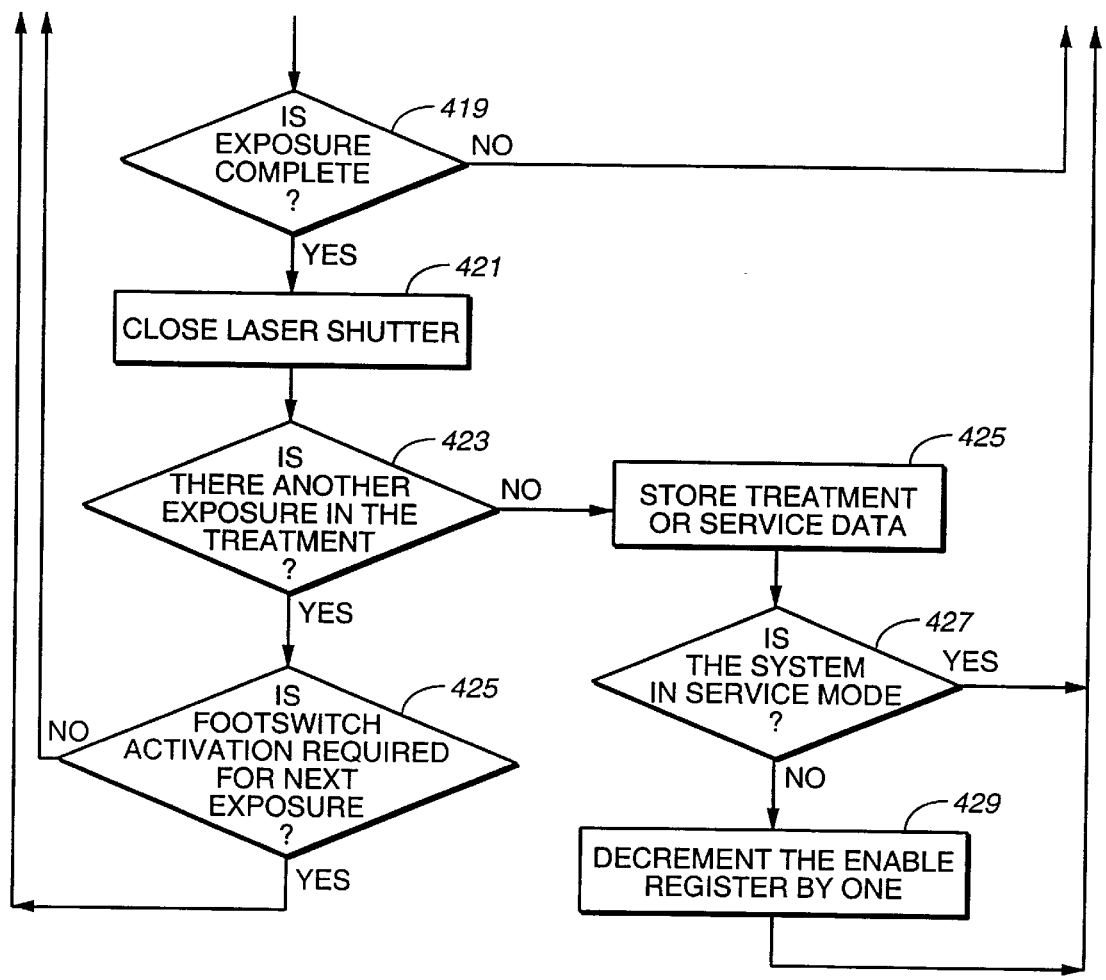
FIG._13C
FIG._13
FIG._13A
FIG._13B
FIG._13C

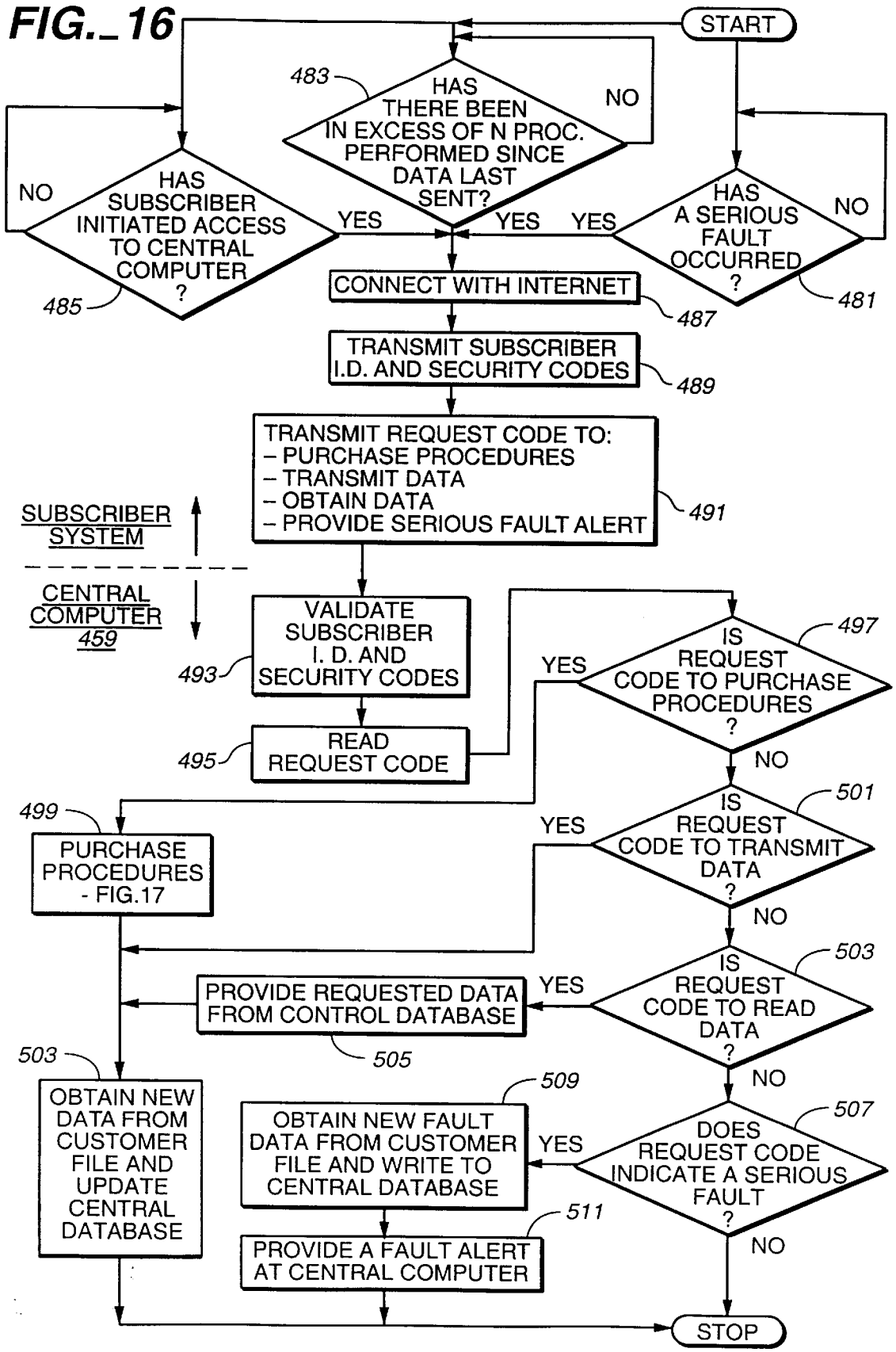
FIG._16

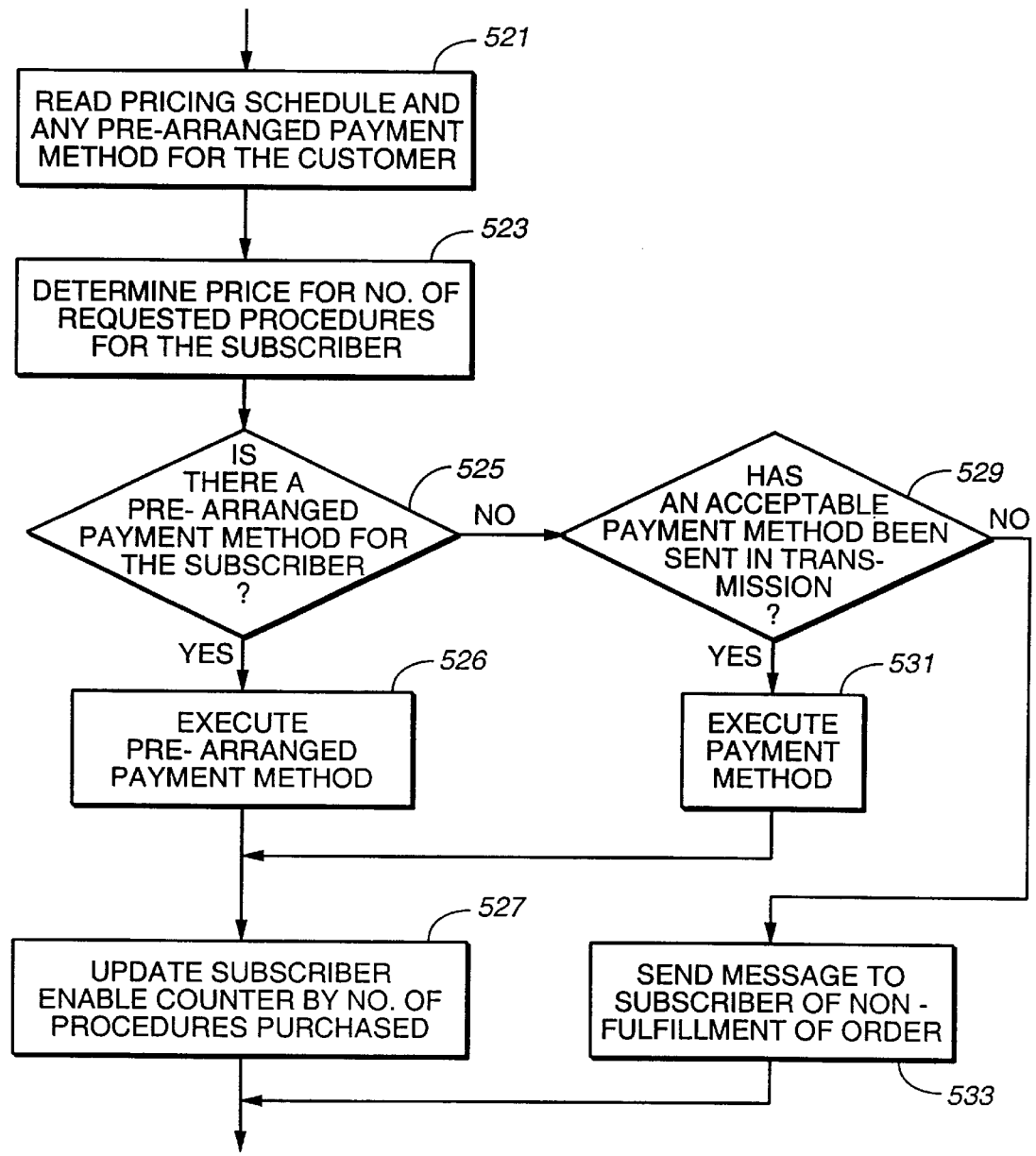
FIG._17

METHOD AND APPARATUS FOR EXPOSING A HUMAN EYE TO A CONTROLLED PATTERN OF RADIATION

BACKGROUND OF THE INVENTION

This invention relates generally to techniques of exposing an eye to electromagnetic radiation for the purpose of treatment, and, more specifically, to an improved apparatus that controllably directs a defined pattern of electromagnetic radiation to a cornea for the purpose of reshaping the cornea.

Although there are many specific treatment procedures involving the necessity for directing a highly controlled beam of electromagnetic radiation to an eye, keratoplasty procedures are currently receiving a great deal of attention because of their ability to correct an eye for nearsightedness, farsightedness and/or astigmatism. In one surgical procedure, a radiation beam is used to cut controlled portions of the cornea by ablation of tissue in its path. One specific application of this procedure is in the performance of a radial keratotomy procedure without the necessity of using a knife to make radial cuts in the cornea. In another specific application, an outside surface of the cornea removed by an eximer laser in order to reshape it.

An alternative procedure, which avoids cutting the cornea, directs one or more focused beams of electromagnetic radiation within the infrared portion of the spectrum into the eye to thermally shrink collagen tissue within the cornea in order to cause corrective changes in the cornea curvature. This later technique, often termed photothermal keratoplasty (PTK), is the subject of U.S. Pat. Nos. 4,976,709 and 5,618,284 to Dr. Bruce J. Sand, which patents are expressly incorporated herein in their entirety by this reference. The collagen shrinkage technique promises to provide permanent changes to the optical characteristics of the human cornea with a higher degree of safety and patient comfort than is the case with techniques that involve physically cutting and removing portions of the cornea.

One way to deliver a desired electromagnetic radiation pattern to the cornea is by projection from a short distance removed from the cornea. One instrument for doing so is described in international PCT application publication no. WO 94/03134 (hereinafter "PCT Publication"), which publication is hereby incorporated herein in its entirety by this reference. That described instrument allows an ophthalmologist, or other attending physician or practitioner, to select and deliver a specific pattern and amount of electromagnetic radiation to each patient in accordance with the condition to be corrected. It is desirable for such an instrument to efficiently perform corrective photothermal keratoplasty procedures on a large number of patients with a high degree of accuracy, effectiveness, safety and convenience.

Therefore, it is also an object of at least one aspect of the present invention to provide an instrument, including but not limited to the type of the PCT Publication, that operates with a high degree of accuracy, effectiveness, safety and convenience to project controlled patterns of treatment radiation onto a cornea being treated.

It is another object of at least one aspect of the present invention to provide a system, including but not limited to the type of the PCT Publication, for remotely linking a number of geographically dispersed medical treatment instruments with a central computer database for useful purposes.

It is a further object of at least one aspect of the present invention to provide an improved method and system, including but not limited to the type of the PCT Publication, for projecting a controlled pattern of infrared radiation against the cornea of the eye in performance of photothermal keratoplasty procedures.

SUMMARY OF THE INVENTION

Accordingly, many individual improvements have been made in the treatment system described in the PCT Publication, including individual improvements which may be either implemented by themselves or together in cooperation with one another. The system described herein with respect to the preferred embodiments generates, as does the system of the PCT Publication, a ring of treatment radiation spots by directing a single laser beam through a multi-faceted prism element. Although some of the individual improvements of the present invention are specifically directed to that type of system, others are not so directed but rather also have application to many other types of radiation delivery systems.

According to one aspect of the present invention, briefly and generally, many of the improvements make the treatment system easier to use with precision. An example is a headrest with a sensor that provides an indication to the treating physician of the distance of the patient's forehead from the treatment instrument and even prevents the instrument from emitting treatment radiation if that distance is too great. Another example is the use of an eye tracker that compares the rotational position of the eye being treated with a reference position, being able to adjust the radiation pattern to compensate for small eye movements and preventing the instrument from emitting treatment radiation if that movement is too great. Both of these features are useful individually but together monitor movement of the eye being treated in all three axes and prevent treatment radiation from being directed against that eye when it has moved out of its proper position. Another example of an improvement is the use of two monochromatic light beams emitted from the front of the instrument in a manner to cross each other and form a single spot at the optimal position of the eye being treated, thereby allowing easy adjustment of the instrument optics to a position that is an optimal distance from the eye being treated. A further example of an improvement includes a heads-up display that provides information to the attending physician without the physician having to interrupt his or her view of the patient's eye through the instrument.

According to another aspect of the present invention, a system of the type described in the PCT Publication, which is limited in the variety of radiation patterns that can be controllably directed against the eye being treated, has been improved with an electronic control system that allows that type of system to generate a wide variety of radiation patterns by use of sequential exposures to all or less than all of the ring of spots being formed with different diameters. Each treatment procedure is pre-programmed by storing, in the electronic system, parameters for each of one or more sequential exposures that each provide a radiation pattern that has been determined to be best for providing the desired vision correction. Once the optics of the system have been properly aligned to the eye being treated, the electronic control system causes the optics to adjust to specific geometric parameters before each of a plurality of exposures. The result is an ease of use of the system, accuracy in generation of the composite radiation pattern and the generation of multiple exposures in a small amount of time. This allows the attending physician to direct against the patient's eye being corrected practically any treatment radiation pattern believed best to effect the correction.

According to a further aspect of the present invention, the intensity of the treatment radiation is automatically calibrated before treatment begins. A radiation detector is moved into the path of the treatment radiation near to the patient's eye being treated and then removed out of the way. A first test is made of the entire treatment radiation pattern to calibrate a photodetector that is provided as part of the treatment laser system. A second test is made by measuring different portions of the pattern, comparing these intensity readings and then balancing them in order to balance the intensity of the pattern.

According to yet another aspect of the present invention, treatment systems located in geographically separated offices of treating physicians are linked by communications links, preferably over the Internet, to a common data processing center. This center can serve one or more of a number of functions. One such function is the payment of fees. It is contemplated that the attending physicians pay a fee to the operator of the center for each procedure that they perform on a patient with their systems operating properly. To easily allow pre-payment of such fees, each system is provided with a pre-payment counter as part of its electronic control system. Each time a procedure is satisfactorily performed, the count of the counter is changed to reflect one less pre-payment. If the counter shows no pre-payments have been made, the system electronic control system will not allow the system to perform a procedure. The offices of an attending physician can easily update this counter over the Internet by forwarding a request to the data processing center, which then processes the request by automatically referring to a table that contains information of authorized methods of charging the cost of the requested number of procedures being purchased. If the requested purchase is thus allowed, the data processing center sends back over the Internet signals that add the purchased number of procedures to the purchaser's system counter. The purchaser is similarly automatically charged for the purchase.

Another example of a use of the data processing center is to gather information of various types from the system users which, in turn, is accumulated in a central database that is made accessible over the Internet by all subscribers. The parameters and settings of each system are automatically stored in the system's memory after successful completion of the procedure. The results of pre-procedure and post-procedure patient examinations may also be stored by the attending physician in his/her system memory. These data are then automatically transmitted to the data processing center and put together to form a database of a large and increasing number of patients. This experience database is then made available for use by the contributing system users.

According to an even further aspect of the present invention, alternative to use of the Internet, a smart card is used to pre-pay for use of the instrument for treatment procedures. Such an active electronic credit card sized device is programmed by a central licensee to authorize one or more procedures to be performed by a particular instrument. When that card is inserted into the specified instrument, the instrument is unlocked to perform one or more procedures. Data from those procedures are also transferred from the instrument to the card for storage.

Additional objects, advantages and features of the present invention will become apparent from the following description of a preferred embodiment thereof, which description should be taken in conjunction with the accompanying drawings.

BRIEF DESCRIPTION OF THE DRAWINGS

FIG. 1 is a perspective view of an ophthalmic treatment instrument from a side that faces an attending physician;

FIG. 2 is a perspective view of the instrument of FIG. 1 from an opposite side that faces a patient;

FIG. 3 is a side view of the instrument of FIGS. 1 and 2 with typical positions of a patient and attending physician being outlined;

FIG. 4 is a close up of the view of FIG. 2 of the instrument of FIGS. 1 and 2, with a patient headrest removed;

FIG. 5 is a simplified schematic diagram of the optical system within the instrument of FIGS. 1 and 2;

FIG. 6 is a drawing of a typical human eye, for reference;

FIG. 7 is an illustration of certain exposure parameters of the instrument of FIGS. 1 and 2, when used with the human eye of FIG. 6;

FIG. 8 is an expanded view of an electro-optical system within the instrument of FIGS. 1 and 2;

FIG. 9 is a schematic block diagram of the electronic system within the instrument of FIGS. 1 and 2 that operates in conjunction with the electro-optical system of FIG. 8;

FIG. 10 is a sample format of settings of the instrument of FIGS. 1 and 2 that provide selected degrees of correction to the vision of a patient;

FIG. 11 is a flow chart that illustrates a method of automatically calibrating the instrument of FIGS. 1 and 2;

FIG. 12A schematically illustrates a circular radiation dot pattern with an x-y axis superimposed;

FIG. 12B illustrates an adjustment of an end of an optical fiber that occurs in the electro-optical system of FIG. 8 as part of a calibration;

FIG. 13 is a flow chart showing operation of the instrument of FIGS. 1 and 2 to expose an eye to an electromagnetic radiation pattern;

FIG. 14 is a block schematic diagram showing individual physician office networks and a common connection to a central service provider computer through the Internet;

FIG. 15 illustrates an individual instrument database that is maintained both at the physician location and the central computer;

FIG. 16 is a flow chart that illustrates a method of communication between physician offices of FIG. 14 and the central service provider computer; and FIG. 17 is a flow chart showing operation of the procedure purchase block of FIG. 15.

DESCRIPTION OF A PREFERRED EMBODIMENT

The various aspects of the present invention, those summarized above and others, are illustrated herein to be implemented in a system that corrects vision by photothermal keratoplasty. The system is easily configured to precisely generate a desired pattern of electromagnetic radiation to correct a vision deficiency, such as far-sightedness, of a particular patient. The specific type or amount of vision correction required by the particular patient determines the specific configuration for that patient. Many aspects of the present invention are also applicable to other techniques of eye vision correction, wherein certain parameters are different, such as the treatment radiation wavelengths, patterns, exposure times, and the like. Further, many aspects of the present invention are applicable to the generation of radiation patterns for other uses than correcting vision. Additionally, many aspects of the present invention are applicable to operation of a wide variety of medical treatment or diagnosis systems.

The example instrument will initially be generally described with respect to FIGS. 1–4. By way of convenience, the system is described herein with reference to terms which correspond to a representation 80 (FIG. 1) of a three-dimensional Cartesian coordinate system, including an x-axis, a y-axis, and a z-axis. Right, left, lateral, horizontal, or like movement is in a direction substantially parallel to the x-axis, up, down, elevational, vertical, or like movement is in a direction substantially parallel to the y-axis, and fore, aft, proximity-adjusting, or like movement is in a direction substantially parallel to the z-axis.

This instrument is specifically designed for use in an office of an ophthalmologist, other physician or medical service provider, where reliability and ease of use are important since technical assistance is not on site or very close to the office. A base 11 is provided with casters for ease of movement of the system within the office. A table assembly 13 is carried by the base in a manner to be adjustable up and down with respect to the base by a motor (not shown in FIGS. 1–4) within the base. This allows vertical adjustment of an optical radiation delivery instrument 15 to suit a physician 17 that is performing the procedure and a particular patient 19 who is having his or her vision corrected. This adjustment, along with a usually independent adjustability of physician and patient chairs 21 and 23, permits comfortable positioning of both the physician and patient with respect to the instrument 15. Handles 20 and 22 on opposite sides of a top 25 of the table of the assembly 13 make it easy to move the system by rolling on its casters.

The radiation delivery instrument 15 is carried on the top 25. During the procedure, the physician looks through binoculars 27 on one side of the instrument 15 and a treatment optical radiation pattern exits the other side of the instrument through an opening 29. This radiation is directed through a few inches of air to a patient eye 31 being treated. Only one eye is treated at a time in one procedure. In order to hold the treated eye in a fixed position with respect to the table assembly 13, a headrest assembly 33 is attached to the table top 25. The headrest assembly 33 is described in more detail in a copending patient application of Herekar et al, entitled "Apparatus and Method for Receiving the Head of a Subject, and System and Method for Treating Tissue in a Region of the Head of a Subject," field concurrently with the present application, which copending application is incorporated herein in its entirety by this reference.

Briefly, in one operational embodiment, the patient's head is placed in contact with the assembly 33 in preparation for or during treatment. The head is optionally urged against the assembly 33 such as by being strapped against it. A transducer 35 is built into a top of the headrest assembly 33 in a position to be contacted by the forehead of the patient. This transducer provides an electrical signal with a magnitude related to a degree of contact between the patient's forehead and the assembly 33. By way of example, the degree of contact, and thus, the electrical signal, may be related to an amount of pressure or force applied to the assembly 33 when the patient's forehead contacts the assembly. The resulting electrical signal is used to confirm an appropriate level of contact, or to indicate an inappropriate level of contact, between the patient's forehead and the headrest assembly. Thus, this electrical signal is usefully fed into an electronic control portion of the system that, for example, may provide a desired safety response.

Once the patient's head is placed against the headrest assembly 33, the radiation pattern from the opening 29 is manually aligned with the eye 31 by movement of the optical instrument with respect to the table top 25. The physician so moves the instrument by manipulating a joystick type of handle control 37 on a base 39 of the instrument. The handle 37 operates a mechanism (not shown) positioned under the base 39 of the instrument 15 that, in response to movement of the handle 37 to the left or right by the physician 17, moves the projected radiation pattern between the patient's right and left eyes and horizontally adjusts the pattern on the selected eye 31 being treated. Movement of the handle 37 forward and backward by the physician 17 moves the instrument 15 toward and away from the patient, respectively, to control the focus of the radiation pattern on the eye 31 being treated. Vertical motion of the instrument 15 with respect to the table top 25 is not provided in this example, but could also be provided. Rather than moving the instrument 15 up and down with respect to the table top 25, the vertical position of the patient eye 31 being treated is controlled by a mechanical adjustment of the headrest assembly 33, as described in the above-referenced copending application.

Included as part of the optical instrument 15 is an illuminator 41 that directs light through a top prism 43 to the patient eye being treated from a side of the eye. This illuminates the eye so that the physician 17 may have a clear view of it through the binoculars 27 when carrying out the treatment procedure. The illuminator 41 is rotatable by hand with respect to the instrument 15 about an axis 45 (FIG. 4). The attending physician may easily adjust the angle of the eye illumination, while looking through the binoculars, in order to obtain a good view of the eye being treated. The illuminator 41 will generally be rotated to one side or the other, depending upon whether the right or left eye of the patient is being treated. Since the prism 43 directs light from about the same height as the treatment radiation output 29, it is rotated out of the way when treatment radiation is directed against the patient eye 31. The intensity of light from the illuminator 41 is adjusted by the physician through rotation of a knob 47 on the base 39 of the instrument.

The base 11 includes a number of electrical receptacles for connection to power and communications systems. Included are a receptacle 49 for a power cord, a receptacle 51 for a telephone line and a receptacle 53 for a local area network (LAN). Several controls and devices are provided on the physician's side of the table assembly 13. These include a key-operated power switch 55 and an emergency button 57 that turns off the treatment radiation source. A floppy-disk drive 59 is also positioned on a side of the table facing the physician. A compact-disk (CD) drive 61, a high-capacity, removable-disk drive 63 and a slot of a card interface 65 for removably receiving an electronic card are also provided. Many of the radiation sources used in the system and a controlling computer are installed in the base unit 11. A foot switch 67 is provided for the physician to use to start treatment after the system is adjusted for a particular patient eye.

A primary input/output device to the system's controlling computer system is a touch-sensitive screen 69. It can be mounted to the table top 25 on either the right (as shown) or left side of the physician, by attachment to respective receptacles 71 and 73. Thus, the attending physician may select whichever side is the most convenient. A usual computer keyboard may also be connected to the internal computer system through a receptacle 75 in the base unit 13 but will unlikely be used by the physician to perform treatments since the touch screen 69 is usually preferred. A tray (not shown) can be added to extend the table top 25 to support a keyboard. A keyboard will be useful when a significant amount of data are input or retrieved through the treatment system, rather than though another computer connected in a LAN with the treatment system. Standard computer-peripheral receptacles 76 and 78 are also provided for connection to an external printer and monitor, respectively.

Referring to the enlarged view of the patient's side of the optical instrument 15 in FIG. 4, with the headrest removed, a radiation detector assembly 79 is provided for calibration prior to treatment. The assembly 79 rotates from an open position shown in FIG. 4, which allows the treatment radiation to be directed against the patient eye through the opening 29, to a closed position (shown in dotted outline in FIG. 8) where the assembly 79 covers the opening 29. When in the closed position, the entire treatment radiation pattern is directed form within the instrument 15 onto a single radiation detector mounted on the inside of the assembly 79. Two spot projectors 81 and 83 are positioned on either side of the opening 29 to aid in focusing the instrument. Each spot projector focuses an output from an optical fiber onto the cornea. An input to these optical fibers can be any bright light source (not shown), such as a green helium neon (HeNe) laser or a green diode pumped frequency doubled neodymium doped yttrium aluminum garnet (Nd:YAG) crystal laser. Four light emitting diodes (LEDs) 85, 87, 89 and 91 are also positioned at corners of a square symmetrically positioned around an outside of the opening 29. These LEDs are usable to calibrate an eye tracker feature that may be included as part of the system. When included, an eye tracker camera 92 views the eye being treated and provides an electronic signal related to the position of the eye. It is particularly useful to monitor any motion of the eye during treatment. Eye tracker systems are commercially available.

Before describing the optical system within the instrument 15 in some detail with respect to FIG. 8, a simplified schematic diagram of certain components of that optical system is provided as FIG. 5. Treatment and aiming laser radiation sources, along with radiation pattern adjusting optics, are indicated together as a block 93, being described below with respect to FIG. 8. Radiation from these sources is directed in a selected pattern as a beam 95 to a treatment dichroic mirror 97, where it is reflected along a path 99 through an objective lens 101 onto the eye 31 of the patient. The focusing spot projectors 81 and 83 are oriented for their beams to cross at the image surface of the objective lens 101. This surface is desired to be superimposed on the surface of the patient eye being treated. To focus the system in advance of performing a treatment, the instrument 15 is moved back and forth, toward and away from the patient, by the physician operating the handle 37 after the patient's head has been positioned in the heat rest 33 and immobilized by it. When the two beams of the focusing spot projectors 81 and 83 reflect from the eye as a single spot, the instrument is appropriately focused. If two spots are reflected, the physician knows that the system is not focused on the eye to be treated. The instrument 15 is then moved either away from or toward the patient, until a single spot indicating focus is obtained. The optical system also includes an LED 102 in the optical path 99. The patient is requested to fix his or her gaze on the LED 102 during preparation for and execution of the procedure.

The physician 17 views the patient's eye 31 along the optical path 99 through the mirror 97 and beam splitters 103 and 105. The beam splitter 103 directs a portion of the light returning along the path 99 into a video camera 107 that allows video recording of the procedure. A liquid crystal display (LCD) 109 is driven by the system computer and displays in one of the binoculars 27, but preferably not both, certain information of the treatment that is useful to the attending physician. This reduces the frequency of the instances when the attending physician needs to avert looking through the binoculars 27 during preparation for and during treatment. Information which can be presented in such a heads up display include the status of the system, magnitude of the headrest sensor 35 signal, whether or not the eye tracking system is locked onto the patient's eye, and the amount of treatment time remaining. This display is positioned in the physician's field of view so as not to interfere with a view of the patient's eye.

For photothermal keratoplasty, the wavelength of the treatment radiation is in the infra-red region of the electromagnetic radiation spectrum, use of a holmium doped yttrium-aluminum-garnet (Ho:YAG) crystal laser having a coherent radiation output with a wavelength of about 2.1 microns being preferred. Since this is not visible, an aiming light beam is superimposed on the treatment radiation beam. The physician then views in the visible region the form of the treatment radiation pattern. The aiming radiation can be in the red region and generated by a laser diode. The fixation LED is selected to emit in the green region, in this specific example. The illuminator need not be monochromatic and emit light in any region of the visible spectrum, but blue or green is preferred.

Referring to FIG. 6, the major visible elements of the patient's eye 31 are given for reference. Between upper and lower eyelids 111 and 113 are the sclera 115, iris 117 and pupil 119. Covering the iris and pupil is a transparent cornea whose outside curvature is changed by shrinkage of collagen within it according to the pattern of infra-red radiation directed against it. Referring to FIG. 7, an example is given of a region 121 in which treatment radiation is directed to correct for hyperopia (far sightedness) and/or astigmatism. The region extends from an inner diameter $d_1$, which is about 5 mm (greater than that of the pupil, which is about 3 or 4 mm), to an outside diameter $d_2$ of around 7 mm, but which can extend outwards to about 9 mm.

In the specific instrument example being described, the treatment radiation pattern at any one time has a maximum of eight radiation spots. The eight spots are symmetrically distributed around a circumference of a circle, separated from each other by 45 degrees. A center of this circle is coincident with the center of the pupil 119 and has a diameter $d_s$ that is adjustable between the diameters $d_1$ and $d_2$ of the exposure region 121. The rotatable position of the spot pattern is also adjustable to an angle θ over a range of from −22.5 to +22.5 degrees from a radial reference 123. The diameter of each spot can also be made an adjustable parameter of the radiation pattern but it is not in the system being described because it has been found to have little effect upon the results. Each of the eight spots is independently turned on and off in the instrument being described. A typical procedure includes multiple exposures to different patterns of spots. This allows the instrument to generate an almost unlimited number of different composite radiation patterns as the result of multiple exposures.

The optical system of the system being described is shown in more detail in FIG. 8. A pulsed Ho:YAG treatment laser 125 and continuous aiming laser diode 127 are located in the base 11 of the system. Their output beams are combined by a dichroic mirror 129 into coincident beams that are coupled with an end of a length of optical fiber 131. That optical fiber extends from the lasers in the system base 11 up into the bottom of the instrument 15. The remaining optical elements of FIG. 8 are in the instrument 15 on top of the table surface 25. The optical fiber 131 maintains an uninterrupted optical path when the top unit 13 is moved up and down with respect to the base unit, and as the instrument 15 is moved with respect to the table top 25 to adjust to a particular patient.

A sub-assembly 132 contains two primary pieces. One is a shutter assembly including eight triangularly shaped shutters 133–140, one for each of the eight radiation spots that may be generated. These shutters are all shown to be closed in FIG. 8. Direct current (d.c.) motors 143–150 are individually connected to open and close the shutters 133–140, respectively. Treatment and aiming laser light exiting the optical fiber 131 is directed against the shutters and then, for those shutters that are opened, onto a polyprism 153. The polyprism 153 has eight substantially flat surfaces on one side that forms a pyramid, generating one of the eight treatment spots from each of the flat surfaces. The shutters and the polyprism surfaces are maintained aligned with each other and are rotated together by a d.c. motor 155 to adjust the pattern angle θ. Another d.c. motor 157 moves the polyprism 153 along an axis 159 with respect to fixed position collimating optics 161 to adjust the diameter $d_s$ of the treatment spot pattern. Added details of the shutter mechanism and the polyprism are contained in the above-referenced PCT Publication.

The size of each treatment spot is adjusted by a stepper motor 163 that controls the distance between the end of the optical fiber 131 and the collimating optics 161. The relative intensity of the eight treatment spots is adjusted by two stepper motors 165 and 167 that move the optical fiber end in orthogonal directions with respect to the polyprism 153. Since the extent of this adjustment is very small it is preferable to simply hold the optical fiber end in a fixed position and tilt its direction slightly. In either case, the relative amount of radiation from the optical fiber that strikes each of the eight faces of the polyprism 153 is adjusted.

The treatment radiation pattern beam 95 then follows the path described with respect to FIG. 5. The treatment mirror is rotatable about orthogonal axes extending through its middle by respective d.c. motors 169 and 171. This moves the treatment radiation pattern across the patient eye 31.

The radiation detector assembly 79 is shown in its opened position in solid lines and in its closed positioned in dashed lines. This assembly is rotated about a pivot 173 between open and closed positions by a d.c. motor 175. A radiation detector element 177 is carried on an inside surface of the assembly 79 in order to be positioned in the path of the treatment beam when the assembly 79 is closed. In the specific system being described as an example, the detector 177 is a pyro-electric type that responds to a temperature change caused by absorption of the infra-red energy of the treatment radiation pattern.

Accompanying each of the several d.c. motors in the system of FIG. 8 is at least one sensor (not shown in FIG. 8) that provides a feedback signal of the position of the element being moved by the motor. The signals from these sensors are used by the electronic control system to verify the positions of the individual elements.

FIG. 9 illustrates such an electronic control system, wherein motors, sensors, cameras, controls, receptacles and radiation sources of FIGS. 1–8 are included as blocks identified with the same reference numbers in order to show their electrical connections. The control system includes a computer motherboard 181 of a commercially available type that includes at least one very fast microprocessor, system volatile and non-volatile semiconductor memory, and other components typically included on such a board. The motherboard 181 is connected to an internal system bus indicated at 183. Keyboard and printer ports 75 and 76 are connected to the motherboard 181. Also connected to the printer port 76 is an enable counter 185 that is accessible to the microprocessor to keep track of a number of procedures, for which payment has been made in advance, authorized to be performed by the instrument. After a procedure is successfully performed, the enable counter 185 is decremented by one. When the count reaches zero, indicating that all of the prepaid procedures have been performed, the system is not allowed to perform any further procedures until the count is increased. The enable counter 185 is incremented when payment for one or more procedures is made. The transaction is most conveniently made remotely through a telephone connection to the Internet, as described below.

A peripheral board 187 interfaces the floppy drive 59, the high capacity removable media drive 63, the CD ROM drive 61 and an internal hard disk drive 189, to the bus 183. Similarly, a motor control board 191 connects with the various d.c. and stepper motors described with respect to FIG. 8, and associated position sensors, as indicated. A power control board 193 connects with certain components previously described and others. A block 195 shows connection of a d.c. motor that raises and lowers the table unit 13 with respect to the base unit 11, as previously discussed, and an associated position sensor. A block 197 indicates that various possible interlock switches can be connected to the system. Examples are interlocks on outer panels of the system, and on any door to the room in which the procedure is being performed on a patient eye. When any such interlock is opened, for example, any treatment can be terminated. A coolant pump 199 circulates liquid in a cooling system of the treatment laser 125.

The treatment laser 125 is also schematically represented in FIG. 9. A circuit board 201 interfaces various components of the laser 125 with the system bus 183. The laser 125 includes a typical laser cavity 203 including solid state lasing material. An output beam 205 exits one end of the cavity through a partially transparent end mirror. A shutter 207 is moveable between a closed position, where it blocks the beam 205 from leaving the laser, and an opened position. A motor source providing that movement is driven by a signal from the circuit board 201, and a sensor of its position (not shown) provides a signal to the board 201. A beam splitter 209 directs a small proportion of the laser output intensity onto a photodetector 211. A second photodetector 213 receives a small output signal through an end mirror at the opposite end of the laser cavity. Signals from the photodetectors 211 and 213 are used to monitor the energy output of the laser beam.

The laser 125 is a pulsed laser, the treatment preferably being performed by generating a series of successive pulses of each radiation pattern directed against the eye. Although it is possible to use a continuous wave laser instead, the example being described uses a pulsed laser. A flash lamp 215 causes the solid state laser material (Ho:YAG in this example) within the cavity 203 to emit a pulse in response to each flash. The flash lamp 215 is driven by a power supply 217 with an energy level specified by a control signal from the circuit board 201. The energy output of each laser pulse is thus also controlled by such a signal. The flash lamp 215 preferably operates at a fixed frequency, such as five kilo-Hertz in this example, thereby also to generate laser pulses at a frequency of 5 kHz.

The laser 125 is liquid cooled, with the pump 199 circulating a coolant therethrough. A sensor 219 provides a signal to the board 201 of the flow of this coolant, and a sensor 221 a signal of its temperature. These two sensor signals allow detection of a malfunction of the pump 199 and/or an excessive temperature of the coolant, conditions normally requiring the laser to be turned off.

The touch display 69 is connected to the system bus 183 through an appropriate display card 223. A board 225 interfaces with the eye tracker cameral 92, and is commercially available. A serial I/O board 227 connects the card interface 65 to the system. A card 229 is removably inserted into the unit 65. A modem 231 provides the telephone line connection 51. A network interface circuit 233 connects with the LAN receptacle 53. A video circuit card connects to the video camera 107 and provides a video output at the receptacle 78. An interface circuit 237 connects the signal output of the headrest sensor 35 to the control system so that treatment may be stopped when that analog signal crosses a threshold that indicates the patient head has moved too far away from the headrest. The circuits 237 may also contain an audio oscillator that drives a loud speaker 239 with a variable frequency tone. The frequency of the tone is proportional to the level of the analog signal output of the sensor 35, and thus proportional to the force being exerted by the patient's head against the headrest. This provides immediate feedback to the patient of any movement during the procedure.

A digital input-output (I/O) board 241 connects the foot switch 67 and heads-up display 109 to the system. It also connects to a ready light 243 which indicates to the attending physician when the system is ready to perform a particular treatment.

A table of FIG. 10 illustrates some of the data that are maintained within the data storage capability of the control system of FIG. 10. This data specifies various settings of the instrument that are to be used when treating a patient to bring about a desired correction in that patient's vision. Parameters for three treatments of different types are included for illustrative purposes. In a treatment no. 1, a single exposure is defined that will bring about a certain spherical correction specified in a column 251. Rather than including numbers in each of the columns for this explanation, "xx" is used instead to indicate those columns in which some number is included for the treatment no. 1.

In order to bring about the desired correction, the parameters of the radiation spot pattern defined in FIG. 7 need to be set. The diameter $d_s$ of the ring of radiation spots is specified in a column 253 of FIG. 10, and the angle $\theta$ in a column 255. The number of successive pulses are given in a column 257, any number from one to hundreds or thousands being possible but from five to ten pulses being typical for a single exposure. The amount of energy per pulse is specified in a column 259, this being controlled by the control signal sent to the laser flash lamp power supply 217 by the control circuits 201. The total energy is typically within a range of 25 to 37.5 milli-Joules per pulse. The resulting duration of a pulse from the type of laser being described is related to the square root of the total pulse energy. The duration of each pulse during the treatments described herein is typically around 160 micro-seconds. The wavelength of the treatment radiation and pulse repetition rate are fixed for all exposures, being 2.1 microns and 5 kilo-Hertz, respectively, in the specific example being described.

Eight columns 261 provide an individual indication of whether each of the eight spot shutters 133–140 (FIG. 8) are opened or closed. An "x" in a column is meant to indicate that its respective shutter is opened. In the case of the example treatment no 1, all eight shutters are indicated to be opened. The resulting single exposure for treatment no. 1 is a pattern of all 8 spots shown in FIG. 7 with the position and laser parameters specified in the table.

Example treatment no. 2 is slightly more involved than treatment no. 1 in that two exposures are made in succession with two different radiation patterns. The desired correction is given in column 251 as "yy" with the various instrument settings for the first exposure also indicated by "yy". Parameters for the second exposure are indicated by "zz" in the next line of the table. At least the diameter $d_s$ or angle $\theta$, or both, of the spot patterns will be different between the two exposures. Two circular patterns with different diameters is typical, as is two patterns having the same diameter but with a different angle $\theta$.

In the example treatment no. 3, astigmatic correction is desired, as specified in columns 263 and 265, in addition to spherical correction. Three successive exposures are made with fewer than all eight spots per exposure, as indicated in columns 261. The treatment mirror 97 is also adjustable, as indicated by parameters in columns 267. A composite pattern resulting from the multiple exposures is elliptically shaped if the ring diameter $d_s$ and angle $\theta$ are appropriately chosen for each exposure. Movement of the treatment mirror 97 may also be used to provide another adjustment. A goal in specifying the exposure parameters is to generate the desired composite treatment radiation spot pattern with as few exposures as possible.

Almost any composite radiation pattern can be generated by the specific system being described with a number of separate exposures to one or more spots of radiation in different positions. Lines are formed by placing spots of successive exposures adjacent one another, for example. These lines can be curved or straight.

Although the spot shutters have been indicated to be either fully opened or fully closed by controlling data in the columns 261, the intensity of each spot can also be individually finely controlled by being able to specify in columns 261 a degree to which the individual spot shutters 133–140 are partially opened. This requires more data and a finer control of the spot shutters than when only fully opened and fully closed positions are possible.

The data of the table of FIG. 10 are empirically developed from experience in the actual treatment of human eyes. Initially, such data is available from clinical trials that have been conducted as part of a process to secure approval by the United States Federal Drug Administration of the photothermal keratoplasty refractive correction technique practiced with the instrument described in the previously reference PCT Publication. Ideally, an attending physician need only input to the system, either through the touch screen 69 or an auxiliary keyboard, the numbers of the desired correction for a particular patient that are determined from a usual eye examination of the patient. Software provided within a memory of the control system of FIG. 9 then looks up from the table of FIG. 10, which will typically be permanently stored on the hard drive 189, those inputted correction values in columns 251, 263 and 265. The instrument setting parameters of columns 253, 255, 257, 259, 261 and 267 of the exposure(s) specified for the desired correction are then read from the table and displayed on the screen 69. The attending physician then has an opportunity to change, delete or add various of these parameters prior to performing the treatment, by modifying the parameters through the touch screen 69. Alternatively, the physician may enter parameters of the exposure(s) directly, without first reading those stored in the table of FIG. 10 for the correction desired.

Once the corrective procedure is completed, the control system of FIG. 10 causes the actual parameters used in the procedure to be stored, along with the amount of refractive correction that was intended to be obtained by their use. Over time, a useful database of actual experience by users of the system is built up and stored on the hard disk drive 189. This database is preferably designed to also accept data of examinations of the treated eye both before and after the treatment. Particularly valuable are data of examinations performed at various intervals after treatment. This database is then useful to an attending physician to design a course of treatment for future patients.

As part of the data stored from the patient eye examinations, corneal topographical data can be included. Indeed, a video camera system can be added to the treatment system being described to acquire such data. Such systems are known. An advantage of integrating this with the treatment system is that the physician then has the ability to easily monitor changes that have actually taken place in the outside surface curvature of the patient's cornea as a result of the treatment. Topographical information can be taken at least immediately after the prescribed treatment is completed, thus allowing the physician to provide supplemental treatment, if necessary, in response to that information. Topographical information can also be taken at times during the treatment, such as after each exposure of a multiple exposure treatment protocol.

A technique of calibrating the treatment instrument prior to performing a specific treatment is illustrated in an operational flow chart of FIG. 11. The steps are controlled by system operating software stored within the control system memory. A first step 301 causes the motor 175 to be energized to position the detector assembly 79 from its open position shown in FIGS. 4 and 8 to a closed position shown in dashed outline in FIG. 8. In the closed position, the radiation detector 177 is positioned in the beam path 99 to receive a pattern of infra-red radiation from the treatment laser 125.

A next step 303 causes the spot shutter control motors 143–150 to be energized to fully open their respective shutters 133–140. Prior to this calibration being conducted, the settings of the treatment instrument have been designated by reading nomogram data from the table of FIG. 10 and/or receiving physician input through the touch screen 69, as previously described. A step 305 then sends a signal to the power supply 217 of the treatment laser 125 that is expected to cause the laser to generate pulses having an energy level specified for the first exposure of the treatment. The treatment laser 125 is then turned on to fire a successive number of pulses, as indicated by a step 307. About twenty such pulses are generated and then an average energy per pulse is calculated from the detected signal. As a next step 309, the measured per pulse energy is compared with the per pulse energy level that the laser 125 was directed to deliver.

If that comparison is not within certain limits specified in the calibration software, as determined in a step 311, then the process loops through steps 313 and 315 to perform the steps 307, 309, and 311 again. But before these steps are repeated, the energy of the laser 125 is adjusted in a step 315 by changing a conversion factor stored within the control system of FIG. 9 that determines the power supply to the flash lamp 215 in response to a specific energy output signal being applied to its power supply 217. Steps 307, 309, and 311 are then repeated after that adjustment. If the measured energy is again not within limits, the process is repeated yet another time. But, as indicated by the step 313, this loop is not permitted to be performed endlessly. Rather, after a fixed amount of time has elapsed, and the laser energy level has not been properly adjusted, the processing proceeds to a step 317 where an alert of a malfunction is issued. The response of the system to such an alert can be that it is shut down, the alert displayed to the physician who can decide to override it, pause the calibration which is then resumed later, and so forth. In any event, a record of the alert is stored in a service database for the instrument to enable a service technician to later diagnose any malfunctions of the system. If the controlling software causes the system to shut down in response to such an alert, then a message is preferably immediately communicated over a telephone connection to a service center, so that a technician can immediately deal with the problem.

Once this power level is appropriately calibrated, a next step 319 determines whether there is a second exposure that is planned to be made as part of the treatment. If so, a next step 321 sets the energy level of the laser 125 so that next energy level by sending an appropriate signal to the flash lamp power supply 217. The steps 307, 309 and 311 are then repeated for that new energy level.

When each energy level to be used in the upcoming patient treatment has been calibrated, a next step 323 causes all of the spot shutters 133–140 to be closed by appropriately energizing their respective motors 143–150. The laser 125 is then, in a step 325, caused to generate pulses with one of the energy levels for which it was just previously calibrated. This is because the total energy level with all the shutters opened has already been measured for that laser setting, and thus provides a value for comparison. The treatment laser 125 is then turned on, in a step 327, and the amount of energy striking the detector 177 as a result of those laser pulses is then measured. A next step 329 compares this measured energy with that measured with the spot shutters completely opened. If this most recent measurement is anything higher than a very small percentage (such as less than one percent) of that measured with the shutters completely opened, a situation of excessive shutter leakage has been detected. If that occurs, the processing proceeds to a step 317 to issue an alert detailing the detected condition. It is important, for various reasons, to make sure that the shutters do not excessively leak treatment laser radiation when electrical signals are sent to fully close the shutters. It is particularly necessary to have little or no leakage when performing a laser pattern energy balance test in subsequent steps of FIG. 11.

The first step 331 of an energy balance calibration is to set the energy level of the laser 125 to one of those for which it was just calibrated. One half of the sport shutters 133–140 are closed and the other one-half opened during each of several successive measurements of the amount of laser energy striking the detector 177. FIG. 12A illustrates these steps. Orthogonal x and y axes are superimposed on the eight radiation spot pattern. In a step 333, two measurements are taken, one with the four spots on one side of the x axis being blocked by their respective spot shutters being closed. The other measurement is taken with those shutters then opened and the shutters for the spots on the other side of the x axis being closed. The total energy detected from a series of twenty or so pulses during each of these measurements is then stored, in a step 335. Next, as indicated by a step 337, the same process is performed with the spots on opposite sides of the y axis. The two energy measurements are then stored, in a step 339. Two comparisons are made in the step 341. The first is to compare the two energy measurements taken in step 333 on opposite sides of the x axis. The second is to compare the two measurements taken in the step 337 on opposite sides of the y axis. If the laser energy is perfectly balanced among all eight radiation spots, each pair of energy levels c should be equal.

A next step 343 determines whether these comparisons are within predetermined limits. If not, the process is repeated after first performing steps 345 and 347. In the step 347, an adjustment is made to the optical system to correct for any excessive imbalance of energy levels. That adjustment is accomplished by appropriately energizing the optical fiber end movement motors 165 and 167 (FIG. 8). As shown in FIG. 12B, the motor 165 moves the end 132 of the optical fiber 131 in a direction 165' along the x axis of FIG. 12A. Similarly, the motor 167 moves the optical fiber end in a direction 167' in a direction along the y axis of FIG. 12A. Movement of the end 132 of the optical fiber 131 affects the alignment of the cone of light leaving that fiber end over the planar surfaces of the polyprism 153 (FIG. 8). This cone of radiation is preferably distributed symmetrically over the polyprism 153 in a manner that each of its eight surfaces receives the same amount of radiation intensity. Of course, a certain variation in the intensity level in each of the eight spots is permitted, the step 343 determining whether the variation is within preset limits.

As previously mentioned, instead of physically displacing the end 132 of the optical fiber 131, that end is preferably held fixed while the motors 165 and 167 cause it to tilt slightly in the orthogonal x and y directions to move the cone of emitted light with respect to the polyprism 153.

The laser energy balance calibration loop step 345 also examines how long this aspect of the calibration process has been going on. If a certain preset amount of time has been exceeded, processing proceeds to the step 317 that issues an alert of this particular fault. As an alternative to keeping track of the amount of time in each of the steps 313 and 345, the number of times that the steps and their respective calibration loops have been performed may be monitored and compared with a permitted number of times before the calibration process is effectively aborted.

Whether the calibration is successful or not, all data resulting from it are stored in the service database within the instrument, as indicated by the step 349. Since the calibration is now complete, or has been aborted, the detector assembly 79, in a step 351, is repositioned out of the beam path 99 by energizing the motor 175 to move it back to the position shown in FIG. 4 and in solid lines in FIG. 8. If the calibration has been successful, the instrument is now ready to treat the patient.

A flowchart of FIG. 13 provides an overall outline of the operating steps to prepare the system being described for treatment and then executing that treatment. When the system is first powered up, it will, after some preliminary checks, proceed to a standby mode, as indicated by an initial step 361. The system then looks for a start request to be made by the attending physician pushing an appropriate button on the touch screen 69. This is indicated in a step 363. A next step 365 determines whether or not the instrument is to be used for an actual treatment, or whether is being put through its steps by a service technician for testing or adjustment. This is provided since a next step 367 determines whether the enable register 185 (FIG. 9) shows at least one procedure to have been paid for in advance. If not, and the system is not in a service mode, the system returns to the standby mode 361. But if a service technician is operating the system, the step 367 is bypassed.

A next series of steps performs internal checks on the system to make sure that certain functions are operating properly. A first step 369 sequentially opens and closes each of the spot shutters 133–140 and measures, by sensors associated with them, the amount of time that it takes to open and the amount of time that it takes to close each shutter. These times are then compared, in a step 371, with a maximum time that is permitted for the shutter to either open or close. This maximum time, is, in this specific example, set to be slightly less than a minimum interval between pulses of this laser 125. For the specific laser parameter described above, this maximum predetermined time is about 200 nanoseconds.

If this spot shutter function test is passed, a number of other status checks are performed, as indicated by a step 373. These checks include making sure that all the interlocks 197 are closed, the various lasers and LEDs of the system are operating, the flow and temperature of the coolant of the treatment laser 125 are within limits, and similar matters. A step 375 determines when all of these status checks have passed. If either of the spot shutter open/closed time test or any of these other status checks have not passed, the processing proceeds to a step 377 wherein data concerning the checks is stored in the service database within the control system of FIG. 9. An alert to the fault is then issued, in a step 379, and the status of the instrument is returned to the standby mode 361.

If all of these tests pass, on the other hand, the settings for the system to perform a particular treatment are read from memory, in a step 381. These are the parameters that are described above with respect to FIG. 10. However, the table of FIG. 10 is not read directly, in the usual case, but rather has previously been used by the physician to develop a treatment plan involving one or more exposures to different spot patterns. A resulting nomogram data is then accessed for ready use by the system when required.

A next step 383 causes the treatment laser 125 to begin firing with its shutter 207 closed. After it is confirmed through the photodetector 213 that the laser is indeed firing and from a sensor associated with the shutter 207 that it is indeed closed, the system automatically indicates that it is ready for treatment to begin, as indicated by a step 385. This ready condition is communicated to the attending physician by illuminating the ready light 243 (FIG. 9), or, alternatively, by providing an indication on the display 69.

When in the ready condition, a ready button become illuminated on the touch screen 69 which is pushed by the attending physician to proceed with the treatment. A step 387 indicates that the controlling software is awaiting such an action. When it occurs, the system is calibrated, as indicated by a step 389, in the manner previously described with respect to FIGS. 11, 12A and 12B. After calibration, the system then awaits the attending physician to push the foot switch 67, as indicated by a step 391. If the foot switch is not pushed within a preset time after the ready button is pushed in step 387, as indicated by a step 393, a step 395 occurs which turns off the treatment laser 125 and returns the system to the standby mode 361.

However, if the foot switch 67 is timely activated, a next step 397 records the position of the patient's eye with the eye tracking camera 92. This becomes a reference during the rest of the procedure. That is, the system included with the eye tracker camera 92 establishes x–y coordinate values for the position of the eye at the time the foot switch 67 is activated. This is the most convenient one of three techniques that can be used to calibrate the eye tracking system. Another technique involves, prior to pushing the ready button in step 387, calibrating the eye tracking system while the patient is looking directly at the fixation LED 102. The x–y coordinates of the patient's eye at a time when an appropriate button is pushed by the attending physician then becomes the reference used during the treatment. A more complete reference is obtainable, as the third calibration technique, where each of the LEDs 85, 87, and 91 are illuminated one at a time and the patient is requested to look at each of the illuminated LEDs. While looking at each LED, the x–y coordinates of the patient's eye are stored.

Once the various system parameters of radiation spot geometry, spot shutter positions, and the like, have been set, the shutter 207 of the laser 125 is opened, as indicated by a step 401. Exposure of the eye being treated to successive pulses of infra-red radiation from the treatment laser 125 is thus begun. During the treatment exposure, several checks are occurring of the status and performance of the system. In addition to performing many of the status checks indicated in step 373 at this time, two other checks are optionally being performed. One is with respect to the eye tracker system and the other with respect to the position of the patient's head. Since some physicians may not want to have the eye tracker and heat positions signals potentially affect the treatment, they may be disabled by the physician, though pushing an appropriate button on the touch screen 69.

The eye tracker system provides, almost continuously, the x–y position of the eye being treated which is similarly almost continuously compared with the reference position established in the step 397. In a step 403, if the measured coordinates of eye movement are within limits that can be corrected by a compensating adjustment of the treatment mirror 97, that adjustment is accomplished in a step 405. The treatment mirror 97 is moved by appropriate energization of its two motors 169 and 171. If the eye tracker has not detected movement within this correctable range, a next step 407 determines whether there has been eye movement beyond the correctable range. If so, the treatment laser 125 is turned off and its shutter 207 closed, as indicated by a step 409. Data of the treatment performed until that occurs is then stored, in a step 411, as well as storing the error data in the service database within the system memory.

Two buttons then appear on the touch screen 69 which may be activated by the attending physician, one button being to continue the treatment and the other to abort the treatment procedure. At the same time, the planned treatment exposures are displayed on the screen 69 to show which exposures have been completed, in the case of a multiple exposure treatment, and/or how many pulses of the current exposure were delivered to the eye before the treatment laser was turned off. The attending physician then has enough data to determine whether to resume treatment or terminate it. The system also allows the attending physician to alter the characteristics of the remaining exposures if necessary to compensate for the interruption. For example, if any only a single or a very few pulses of radiation have been delivered at the beginning of an exposure before the laser 125 is turned off, the physician may choose to start over again and deliver the full compliment of radiation pulses. It is a number of successive radiation pulses that seem to raise the temperature of the exposed collagen tissue sufficiently to cause it to shrink.

If, in step 413, the physician pushes the continue button, at next step 415 turns the treatment laser 125 on again and the exposure to treatment radiation is resumed. If the abort button is pushed in the step 413, the system returns to the standby mode 361. In a step 417, the signal from the headrest sensor 35, which is likely analog but can be digital, is being monitored to determine whether it exceeds a predetermined threshold level during treatment. If so, the processing follows the same path of steps 409, 411 and 413 described above. The result of simultaneously monitoring the position of the eye with the eye tracker system and the position of the head with the headrest sensor is to monitor the position of the eye in all three axes, x, y and z. So long as the patient's head remains fixed on the headrest 33 and the gaze of the eye being treated remains fixed on the fixation LED 102, treatment proceeds without interruption. But if there is sufficient movement, the treatment radiation pulses are terminated and the physician is informed with enough information to determine whether to continue the treatment or not and, if so, whether the parameters for the remaining exposures of the treatment need to be changed from what was planned, in light of the interruption.

A step 419 of FIG. 13 represents a continuing inquiry as to whether a given treatment exposure has been completed or not. This involves counting the number of treatment laser pulses in accordance with the number of pulses that are predetermined for the particular exposure. So long as that number of pulses has not been reached, the position checking loop beginning with the step 403 is repeatedly executed. But when the designated number of pulses for the current exposure have been delivered, that exposure is complete. Typically, something like five to ten pulses are delivered in a given exposure. At a fixed frequency of 5 Hz., the treatment takes from one to two seconds between opening of the laser shutter at step 401 and its closing at a step 421.

A next step 423 determines whether there are any remaining exposures planned for the treatment that have not yet been made. If so, a next step 425 determines whether the planned treatment requires a physician to activate the foot switch 67 before subsequent exposure is commenced. If not, the treatment returns to the step 399 where the new set of laser and optical parameters are set for the subsequent exposure. If activation of the foot switch 67 is required, the processing returns to the step 391. In either case, the process repeats the steps described above for the second exposure with different laser and optical parameters having been set.

If there is only one exposure, or if all of the exposures for the treatment have been completed, this is determined in the step 423. When this occurs, the treatment and any service data is stored in the system memory, as indicated by a step 425. A step 427 again determines whether the system is in a service mode, where some or all of the preceding steps have been performed in order to test the system. If in the service mode, the system returns to the standby mode 361. If not, a next step 429 subtracts one prepaid procedure from the enable counter 185. After that, the system returns to the standby mode 361 to potentially be used for another treatment.

Although the treatment system described can operate as a stand alone system, it is preferable to take advantage of data communication techniques to connect all of many geographically dispersed treatment instruments to a common database and service center. It is also desirable, within each physician office where the treatment system is installed, to interconnect it through a local area network (LAN) to the office's personal computer system so that treatment planning and database functions may be carried out from that office computer. Such a system is generally illustrated in FIG. 14. Two physician offices 451 and 453 are illustrated. The office 451 has a treatment system 455, as described above, in a patient treatment room. That office also has a personal computer 457 in another room such as the office clerical or reception area. The system 455 and computer 457 are coupled together by a LAN. The second physician office 453 is similarly equipped, as are a large number of others that are geographically spread throughout the United States and other countries of the world. It is desirable to provide a data-connection between as many of the treatment systems as possible and a central computer and database 459 that is preferably provided in a single location. Connection is preferably made between the central location 459 and the individual physician offices around the world through the Internet 461.

One use of the central database 459 is to permit the individual physicians to access information that is accumulated from all of the subscriber physicians that are connected to the central database. FIG. 15 generally illustrates the type of information that is stored in the treatment system memory of each subscriber physician. A database 463 allows the physician to input the results of examinations of the patient, both before and after the treatment. The database portion 465 automatically receives the various parameters that were used to treat each patient. Another portion 467 of the system database includes data of failures and faults incurred during operation of the treatment system. It is the type of information illustrated in FIG. 15 that is desirably transmitted to the central database 459. The patient related portions 463 and 465 of the databases of all subscribing physicians are put together into a common database that then may be accessed by all subscribers. This is quite useful to assist physicians in choosing a set of system parameters for use in correcting for a certain vision problem that one or more other subscriber physicians may have already used and for which data was generated.

The service database 467 allows centrally based service technicians to review operation of each subscriber treatment system over a long period of time. This assists the service technician to diagnose any specific malfunction that needs attention. In addition, communication from each treatment system provides for immediate notification of a service technician at the central computer location of any fault that is of a serious nature, one which either prevents the given treatment system from operating or indicates the risk of a major malfunction in the near future. The service technician at the location of the central computer 459 then remotely operates a given instrument in its service mode to further diagnose and perhaps even correct the problem without having to visit the subscriber physician's site. However, if a physical visit is necessary, the service technician can arrange it in response to this automatic notification from the ailing system.

FIG. 16 illustrates, by use of a flowchart, communication between an individual subscriber system and the central computer 459. The communication illustrated in FIG. 16 is initiated by the subscriber's treatment system. As part of the computer control of that system, a step 481 monitors whether a serious fault has occurred, a step 483 monitors whether there has been a substantial delay since data was last transmitted to the central computer, and a step 485 monitors whether the subscriber has requested access to the central computer 459. These three inquiries are occurring at the same time. The inquiry 483 is designed to make sure that the subscriber database of the form of FIG. 15 is transmitted to the central computer often enough to keep service technicians properly informed and to maintain the composite patient database that all subscribers reference. When either of the conditions 481, 483 or 485 occur, as indicated by a step 487, the subscriber system is connected with the Internet. Typical subscriber identification and security codes are then transmitted to the central computer, as indicated by a step 489. In a step 491, a particular request is transmitted to the central computer. Examples of the requests to which the central computer 459 can respond are shown. One is to purchase additional procedures which results in the enable counter 185 being updated. Another is to transmit data in the form of the subscriber's database of FIG. 15. Another is to obtain data from the central computer database 459, such as patient information (but without identities of the patients) included in the composite database to which all subscribers contribute. Another is to provide a serious fault alert for a service technician.

At the central computer 459, a step 493 validates the subscriber identification and security codes. A next step 495 reads the request code transmitted from the subscribers system. If that request is to purchase procedures, as indicated by the step 497, a procedure purchase 499, as shown in more detail in FIG. 17, is executed. If the request is not to purchase treatment procedures, a step 501 determines whether the request is for the subscriber to transmit data to the central computer 459. If so, the central computer 459, in a step 503, obtains the transmitted data and updates its composite patient and service databases with it. If the request is not for the subscriber to transmit data, a next step 503 determines whether the request is to read data from the composite database. If so, the central computer 459 provides a requested data, in at step 505.

If the request from the subscriber is not to read composite data, the request is further examined in a step 507 to determine whether the subscriber system has sent an indication of a serious fault. If so, the fault information received is stored in the central service database, in a step 509. Also, a fault alert is provided at the central computer 459, as indicated by a step 511, so that a service technician at the central location can attend to correcting the fault by either remotely accessing the subscriber system or dispatching a service technician to the subscriber location.

The procedure purchase step 499 of FIG. 16 is illustrated in a further flowchart of FIG. 17. When the subscriber requests to purchase procedures, the central computer 459, in a step 521, accesses a subscriber file to read the pricing and/or discount schedule that applies to that particular subscriber, as well as identifying a method that has been arranged with that particular subscriber for making advance payment for treatment procedures. One such prearranged payment method is to charge a particular credit card. Another is to indicate that the subscriber is extended credit and is to be billed for purchase procedures, but perhaps up to a certain number or dollar amount. A next step 523 looks up in the pricing schedule the total price for the number of procedures that is requested by the subscriber to be purchased in this Internet transmission.

In a step 525, it is determined whether there is an acceptable method of payment that has been prearranged with this particular subscriber. If there is one, a next step 526 initiates a charge against the customer by the prearranged payment method. The next step 527 sends to the subscriber system data that updates its enable counter 185 by adding the number of purchases procedures to its count.

If, in step 525, it is determined that there is no prearranged payment method for the subscriber, a next step 529 determines whether some acceptable payment method has been transmitted by the subscriber as part of this Internet communication. The subscriber may request in the transmission that the purchases be charged to a credit card, for example. If such an authorization is provided with the request, a next step 531 checks for authorization with a credit card company, or otherwise verifies that the payment method is proper. The requested procedures are then charged to the credit card or other payment method provided. The processing then proceeds to the step 527. However, if there is neither a prearrange payment method in the subscriber record of the central computer 459, nor an acceptable payment method received with the request, the processing proceeds to a step 533, wherein a message is sent to the subscriber that the order for pre-paid procedures cannot be filled.

As an alternative to transacting prepayment of procedures over the Internet, use of a physical card of some available type may be used. That is, a small electronic card can be used to carry data to the treatment system of a subscribing physician to enable operation of that system. The card is encoded with data to enable one or more treatments to take place. The subscriber purchases the card by paying an amount determined by the number of pre-paid purchases that the card will authorize. The card may be a "smart" card, or any other type that contains rewritable non-volatile memory, such as a flash semiconductor memory card that interfaces with the treatment system with a disk drive protocol. Such a card 229 is illustrated in FIG. 9. It is manually inserted and removed from the card read/write interface 65 with a slot positioned on the side of the table 25 (FIG. 1) facing the attending physician.

Data of the number of pre-paid procedures carried by such a card 229 can be read by the card interface 65 and loaded into the enable register 185 (FIG. 9) of the treatment system. Alternatively, the card itself may be inserted prior to conducting a procedure and directly read by the system when determining whether a procedure has been purchased, and, if so, serve the function of the enable register 185 (step 367 of FIG. 13) to allow a treatment to take place. Data of the number of pre-paid procedures authorized by the card is then rewritten after the procedure is successfully concluded, to reduce the number of prepaid procedures by one (corresponding to step 429 of FIG. 13). One distribution technique is to authorize only one procedure with each card. Each card may then also be used to store all the examination and treatment data for the one patient whose treatment is authorized by it.

Although the various aspects have been described with respect to preferred embodiments thereof, it will be understood that the invention is entitled to protection within the full scope of the appended claims.

It is claimed:

1. In a medical treatment apparatus capable of simultaneously projecting against an eye a plurality of electromagnetic radiation spots spaced around a circumference of a circle, wherein the diameter of the circle and rotatable position of the spots therearound are controllable, a method of treating a patient eye, comprising:

storing, within a memory of the apparatus, at least first and second sets of parameters of exposures of the patient eye for respective at least first and second radiation spot patterns to provide a desired correction of the patient eye, the exposure parameters including radiation energy level, circle diameter, rotatable position of the spots and relative attenuation of the individual spots, causing the apparatus to make adjustments according to the stored parameters of exposure to the first radiation spot pattern, thereafter projecting the first radiation spot pattern against the given patient eye from the apparatus adjusted to the first set of parameters of exposure, thereafter causing the apparatus to make adjustments according to the stored parameters of exposure to the second radiation spot pattern, and thereafter projecting the second radiation spot pattern against the given patient eye from the apparatus adjusted to the second set of parameters of exposure.

2. The treating method according to claim 1, wherein at least the stored spot circle diameter of the first and second spot patterns is different.

3. The treating method according to claim 1, wherein at least the stored relative attenuation of the individual spots of the first and second spot patterns causes there to be fewer spots in one of the first and second spot patterns than in the other.

4. The treating method according to claim 1, wherein at least the stored radiation level of the first and second spot patterns is different.

5. The treating method according to claim 1, wherein at least the stored rotatable position of the first and second spot patterns is different.

6. The treating method according to claim 1, wherein the plurality of radiation spots is generated within the apparatus by directing the radiation from a single source to an optical element having multiple faces, the diameter of the circle of spots is controlled by moving the optical element with respect to the single source of radiation, and the rotatable position of the spots is controlled by rotating the optical element.

7. The treating method according to claim 1, wherein each of projecting the first radiation spot pattern and projecting the second radiation spot pattern includes projecting a plurality of radiation pulses, and the stored first and second sets of parameters additionally include a number of pulses.

8. The treating method according to claim 7, wherein the apparatus automatically terminates exposure of the patient eye to the plurality of radiation pulses upon detecting any one of the conditions of excessive eye movement, excessive head movement, or a change in output level of a source of the electromagnetic radiation.

9. The treating method according to claim 1, wherein a source of the electromagnetic radiation spots includes a laser.

10. The treating method according to claim 1, wherein the plurality of spots projected by the apparatus are within the infra-red portion of the electromagnetic spectrum.

11. The treating method according to claim 1, wherein each of projecting the first radiation spot pattern and projecting the second radiation spot pattern includes shrinking corneal tissue of the patient eye in regions exposed to the radiation spots without causing the exposed regions of corneal tissue to be ablated.

12. Medical treatment apparatus including an instrument capable of simultaneously projecting a pattern of both invisible treatment electromagnetic radiation and superimposed visible non-treatment electromagnetic radiation against a patient eye, comprising:

a guide against which a head of a patient is positionable to hold an eye of the patient that is being treated a controlled distance from the instrument, said guide including a sensor that provides a first signal related to movement of the head with respect to the guide that is away from the instrument, at least one optical element that is moveable to position the radiation pattern across the patient eye being treated, an eye tracker that optically observes a position of said patient eye with respect to a reference and provides a second electrical signal related to a difference therebetween, and a control system that operates in response to the second electrical signal to move said at least one optical element an amount related to the second signal to compensate for eye movement and to prevent exposure of the eye to treatment radiation when either the first signal indicates head movement in excess of a first predetermined amount or the second signal indicates eye movement in excess of a second predetermined amount.

13. The apparatus of claim 12, wherein said at least one optical element includes a planar mirror that is rotatable about orthogonal axes in response to at least said second signal.

\* \* \* \* \*